(12) United States Patent
Kotov et al.

(10) Patent No.: US 9,242,087 B2
(45) Date of Patent: Jan. 26, 2016

(54) NANOCOMPOSITES FOR NEURAL PROSTHETICS DEVICES

(71) Applicant: The Regents of the University of Michigan, Ann Arbor, MI (US)

(72) Inventors: Nicholas A. Kotov, Ypsilanti, MI (US); Huanan Zhang, Ann Arbor, MI (US)

(73) Assignee: The Regents Of The University Of Michigan, Ann Arbor, MI (US)

( * ) Notice: Subject to any disclaimer, the term of this patent is extended or adjusted under 35 U.S.C. 154(b) by 306 days.

(21) Appl. No.: 13/908,806

(22) Filed: Jun. 3, 2013

(65) Prior Publication Data

US 2013/0320273 A1 Dec. 5, 2013

Related U.S. Application Data

(60) Provisional application No. 61/654,529, filed on Jun. 1, 2012.

(51) Int. Cl.
*A61F 2/00* (2006.01)
*A61N 1/05* (2006.01)
(Continued)

(52) U.S. Cl.
CPC .............. *A61N 1/05* (2013.01); *A61B 5/04001* (2013.01); *A61N 1/0529* (2013.01); *A61N 1/0551* (2013.01); *B82Y 15/00* (2013.01); *A61B 5/0095* (2013.01); *A61B 5/055* (2013.01); *A61B 5/061* (2013.01); *A61B 5/686* (2013.01); *A61B 2562/028* (2013.01); *A61B 2562/0209* (2013.01); *A61B 2562/125* (2013.01); *B82Y 30/00* (2013.01); *Y10T 156/10* (2015.01)

(58) Field of Classification Search
CPC ......... A61N 1/05; A61N 1/0551; A61N 1/37; A61L 31/08; A61L 31/16; A61B 2562/125
USPC ........................... 424/423; 433/201.1; 435/14
See application file for complete search history.

(56) References Cited

U.S. PATENT DOCUMENTS 5,207,706 A * 5/1993 Menaker ............... A61L 27/306
604/266
6,428,579 B1 * 8/2002 Valentini ............. A61F 2/30767
427/2.13

(Continued)

OTHER PUBLICATIONS

Shim, Bong Sup, et al., "Multiparameter Structural Optimization of Single-Walled Carbon Nanotube Composites: Toward Record Strength, Stiffness, and Toughness," ACS Nano (2009), 3(7), pp. 1711-1722 (published online Jul. 10, 2009) and Supplementary Information.

(Continued)

*Primary Examiner* — Khanh Tuan Nguyen
(74) *Attorney, Agent, or Firm* — Harness, Dickey & Pierce, PLC

(57) ABSTRACT

Implantable electrically conductive devices are provided having a nanocomposite material coating comprising gold nanoparticles or carbon nanotubes. Such an implantable device may be a neural or other implantable prosthesis, including microelectrodes for use in vivo. The devices may have dimensions on a cellular scale. Further, the devices may be highly flexible and electrically conductive, while also having low impedance and high storage charge capacity. Layer-by-layer methods for fabricating such nanocomposite materials for implantable devices are also provided. Methods for direct-write lithography patterning of such nanocomposite material coatings are also provided.

20 Claims, 21 Drawing Sheets

Figures 1A, 1B, 1C, 1D:
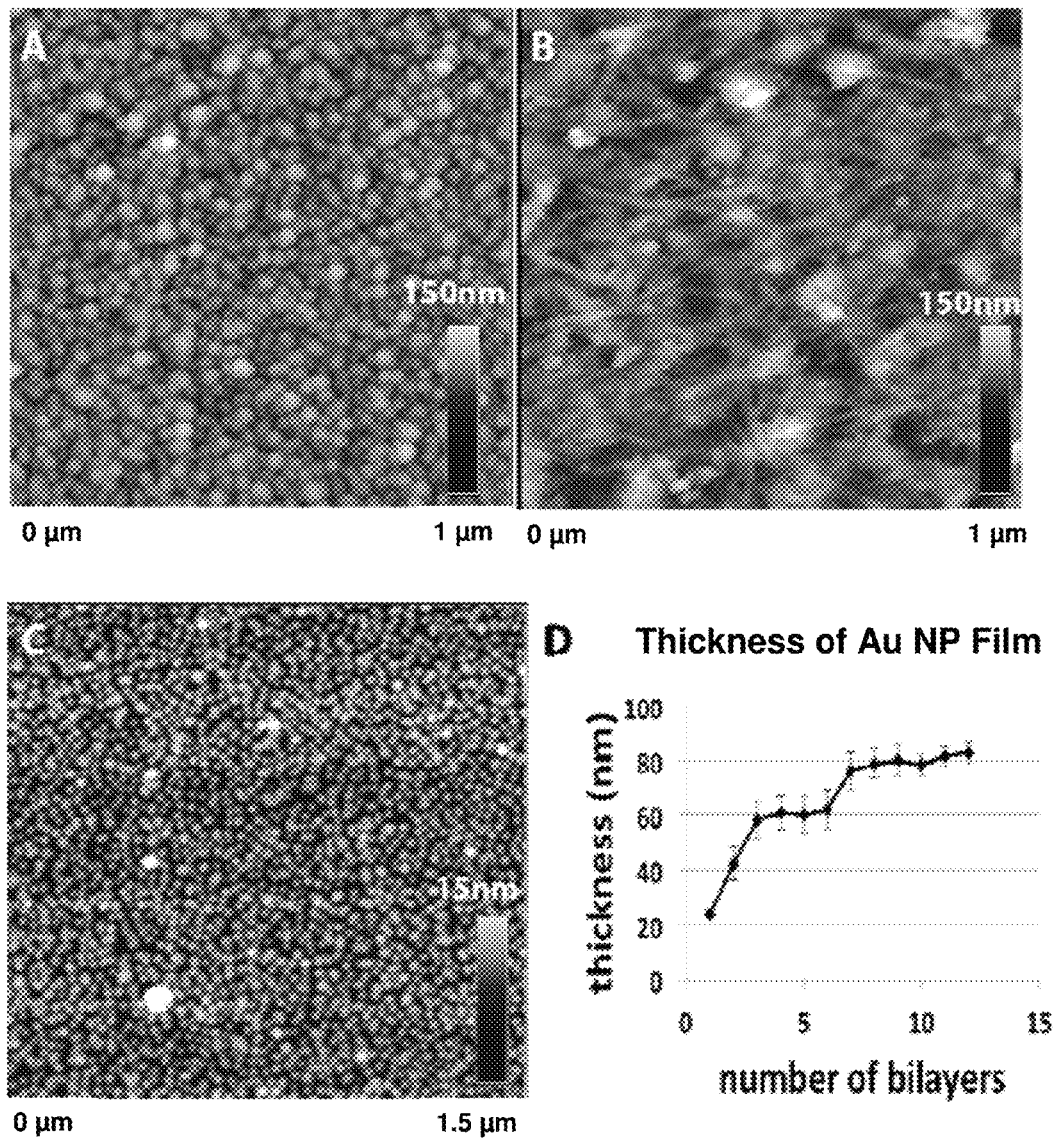

(51) Int. Cl.
*A61B 5/04* (2006.01)
*B82Y 15/00* (2011.01)
*B82Y 30/00* (2011.01)
*A61B 5/00* (2006.01)
*A61B 5/055* (2006.01)
*A61B 5/06* (2006.01)

(56) References Cited

U.S. PATENT DOCUMENTS

2009/0297581 A1* 12/2009 Atanasoska et al. ......... 424/423
2010/0255447 A1* 10/2010 Biris .................... A61C 8/0013
433/201.1

OTHER PUBLICATIONS

Shim, Bong Sup, et al., "Integration of Conductivity, Transparency, and Mechanical Strength into Highly Homogeneous Layer-by-Layer Composites of Single-Walled Carbon Nanotubes for Optoelectronics," Chemistry of Materials (2007), 19(23), pp. 5467-5474 (published online Oct. 10, 2007) and Supplementary Materials.

Zhang, Huanan, et al., "Layered Nanocomposites from Gold Nanoparticles for Neural Prosthetic Devices," Nano Letters, 12(7), pp. 3391-3398 (2012) (published online Jun. 26, 2012) and Supplemental Information.

Bai, Yongxiao, et al., "Direct-write maskless lithography of LBL nanocomposite films and its prospects for MEMS technologies," Nanoscale (2012), 4, pp. 4393-4398 (published online Apr. 18, 2012) and Electronic Supplementary Material.

* cited by examiner

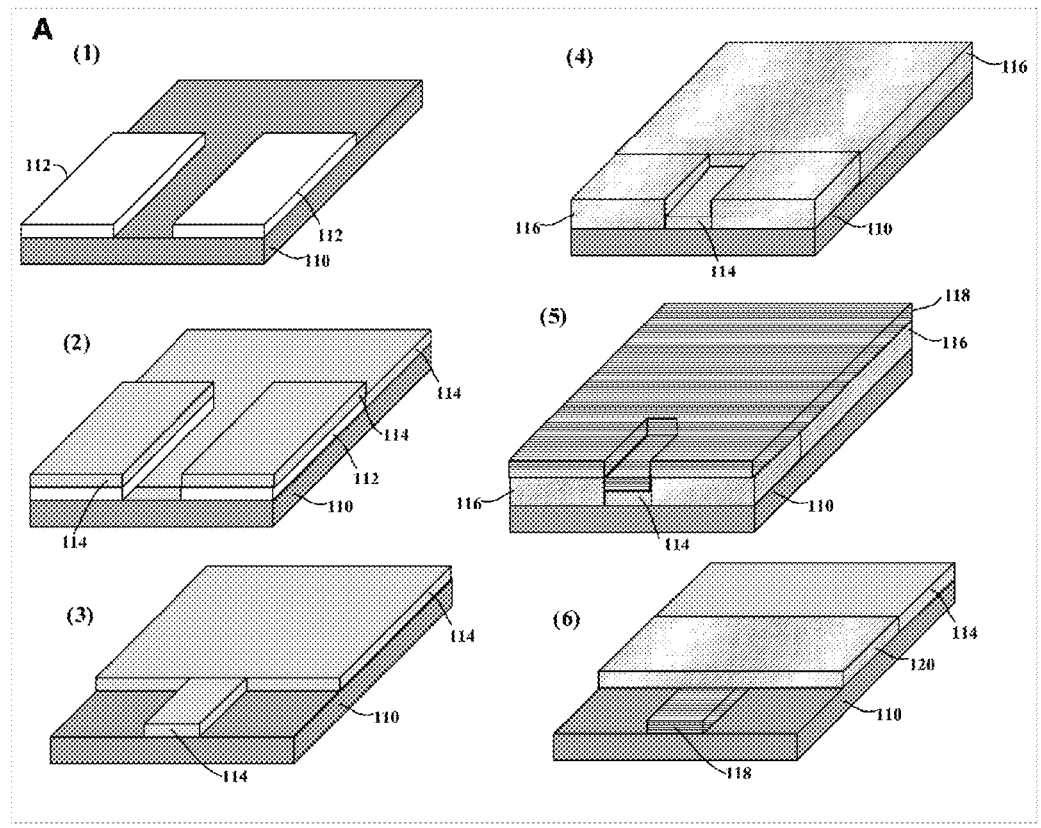
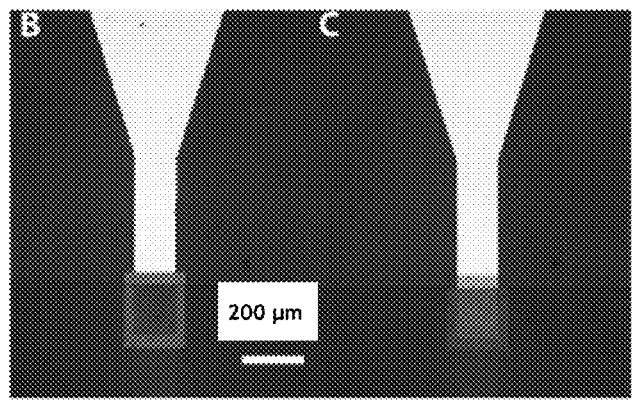
FIGURES 3A – 3C

A

B

C

D

NANOCOMPOSITES FOR NEURAL PROSTHETICS DEVICES

CROSS-REFERENCE TO RELATED APPLICATIONS

This application claims the benefit of U.S. Provisional Application No. 61/654,529, filed on Jun. 1, 2012. The entire disclosure of the above application is incorporated herein by reference.

GOVERNMENT RIGHTS

This invention is made with government support under EB007350 and CA121841 awarded by the National Institutes of Health. The Government has certain rights in the invention.

FIELD

The present disclosure relates to composite materials containing conductive nanoparticles, such as gold nanoparticles or carbon nanotubes that can be used in implantable neural prosthetics devices and methods for making the same.

BACKGROUND

This section provides background information related to the present disclosure which is not necessarily prior art.

Treatments of neurological diseases and the realization of brain-computer interfaces require ultrasmall electrodes that are "invisible" to resident immune cells. Functional electrodes smaller than 50 μm cannot be produced with traditional materials, due to high interfacial impedance at the characteristic frequency of neural activity and insufficient charge storage capacity. Thus, new materials that can form functional electrodes while avoiding the aforementioned issues would be desirable.

SUMMARY

This section provides a general summary of the disclosure, and is not a comprehensive disclosure of its full scope or all of its features.

In certain variations, the present disclosure provides an implantable electrically conductive device, such as a neural prosthetic device, comprising an implantable region that comprises a nanocomposite material. In certain preferred variations, the implantable region of the device is flexible and electrically conductive. The nanocomposite material comprises a plurality of nanoparticles selected from the group consisting of: gold nanoparticles, carbon nanotubes, and combinations thereof. In certain aspects, such implantable electrically conductive devices are mechanically flexible, while also having small dimensions (e.g., similar to a cell size) and also exhibiting the desired electrochemical properties, thus being capable of serving as implantable electrodes with minimal rejection by host tissue, for example.

In other variations, an implantable electrically conductive device is provided that comprises a nanocomposite material disposed on an implantable region of the implantable electrically conductive device that comprises a plurality of gold nanoparticles.

In other variations, an implantable electrically conductive device is provided that comprises a nanocomposite material that forms at least part of a structure of a flexible implantable region of the implantable electrically conductive device. The nanocomposite material comprises a plurality of carbon nanotubes.

In certain variations, the present disclosure provides gold nanoparticle nanocomposites that can successfully be employed in such functional electrodes, like implantable neural prosthetic devices. In certain alternative variations, the present disclosure provides nanocomposites that comprise carbon nanotubes. In certain preferred aspects, the implantable region of the implantable electrically conductive device is formed from the nanocomposite material, which comprises a plurality of carbon nanotubes.

In yet other variations, a method of making a nanocomposite material for an implantable device is provided. The method comprises contacting a region of a substrate with a polyelectrolyte, followed by contacting the region of the substrate having the polyelectrolyte disposed thereon with a solution comprising a plurality of nanoparticles to form a nanocomposite. This process may be repeated as a layer-by-layer process to form a plurality of layers that define a nanocomposite. The nanocomposite may be subsequently further processed (e.g., shaped or patterned via lithographic techniques) to form an implantable region or component of an implantable device. In other variations, the substrate may itself be the implantable region or component, so that the method directly forms a coating comprising the nanocomposite thereon.

In certain variations, a method of making a nanocomposite material for an implantable device is provided. The method comprises contacting a region of a surface of an implantable component with a polyelectrolyte, followed by contacting the region of the surface of the implantable component having the polyelectrolyte disposed thereon with a solution comprising a plurality of gold nanoparticles to form a nanocomposite coating over the region of the surface of the implantable component. This process may be repeated as a layer-by-layer process to form a plurality of layers that define a nanocomposite.

The present disclosure also contemplates methods for preparing an implantable electrically conductive device for implantation into a brain of an animal, as a neural prosthetic device. The method may comprise cooling a flexible, electrically conductive, implantable region and a shuttle within a cold environment, for example, having a temperature of less than or equal to about 0° C. Next, the shuttle and the flexible, electrically conductive, implantable region are heated, so that water condenses on a first surface of the flexible, electrically conductive, implantable region and on a second surface of the shuttle. The first surface is contacted with the second surface and then the shuttle and the implantable electrically conductive device are cooled to a temperature of less than or equal to about 0° C., so as to form a neural prosthetic device assembly capable of implantation into the brain of the animal. Upon implantation, the water between the first and second surfaces will thaw, permitting removal of the shuttle, while the flexible, electrically conductive implantable region of the implantable device remain implanted within the animal's brain.

Further areas of applicability will become apparent from the description provided herein. The description and specific examples in this summary are intended for purposes of illustration only and are not intended to limit the scope of the present disclosure.

DRAWINGS

The drawings described herein are for illustrative purposes only of selected embodiments and not all possible implementations, and are not intended to limit the scope of the present disclosure.

FIGS. 1A-1D: (A) Atomic Force Microscopy (AFM) image of 15 bilayers of Au NP LBL film. (B) AFM image of 25 bilayers of CNT LBL film. (C) First bilayer of Au NP LBL film. (D) Ellipsometric thickness of Au NP LBL films for different number of bilayers. AFM images are obtained using Digital Instrument Nanoscope (R) at a scan rate of 0.5 Hz and tip speed of 30 µm/s.

FIGS. 2A-2F: SEM images of Au NP film and CNT film. Scanning Electron Microscopy (SEM). (A, B) SEM images of Au NP film at different magnifications. (C) Cross-section image of Au NP film. (D, E) SEM images of CNT film at different magnifications. (F) Cross-section image of CNT film. SEM images are obtained using a FEI Nova Nanolab SEM at 10 kV accelerating voltage.

FIGS. 3A-3C: (A) Fabrication process of the microelectrodes with LBL films of Au NPs and CNTs (1) deposition and development of the positive photoresist; (2) E-beam deposition of the metal gold; (3) lift-off of the metal gold layer; (4) deposition and development of the positive photoresist; (5) deposition of the LBL film; (6) lift-off of LBL film and deposition/development of insulating photoresist layer. (B) Optical image of Au NP LBL film-coated electrode. (C) Optical image of CNT LBL film-coated electrode.

FIGS. 4A-4F: Typical electrochemical behavior of Au NP film (red) and CNT films (black). (A) Frequency dependence of impedance, Z. (B) Frequency dependence of the impedance phase angle, $\Phi$. (C) Typical cyclic voltammetry from 0.5 to −0.5 V. (D) Cumulative electrochemical properties of Au NP and CNT films. The data are calculated for sample size of 32 samples. (E) Evaluation of stability of Au NP and CNT films over 500 CV cycles at 1 V/s scan rate for repeating electrochemical excitation. (F) Voltage transient experiment with cathodic current pulses (5 µA, 2 ms).

FIGS. 5A-5D. (A) Circuit analog of the impedance data. (B) Sample confocal fluorescent image of Live/Dead assay (green, Live; red, Dead). (C, D) SEM images of gold nanoparticle (Au NP)/poly(diallydimethylammonium chloride) (PDDA) LBL films before (C) and after (D) insertion into rat brain.

Figures 6A, 6B:
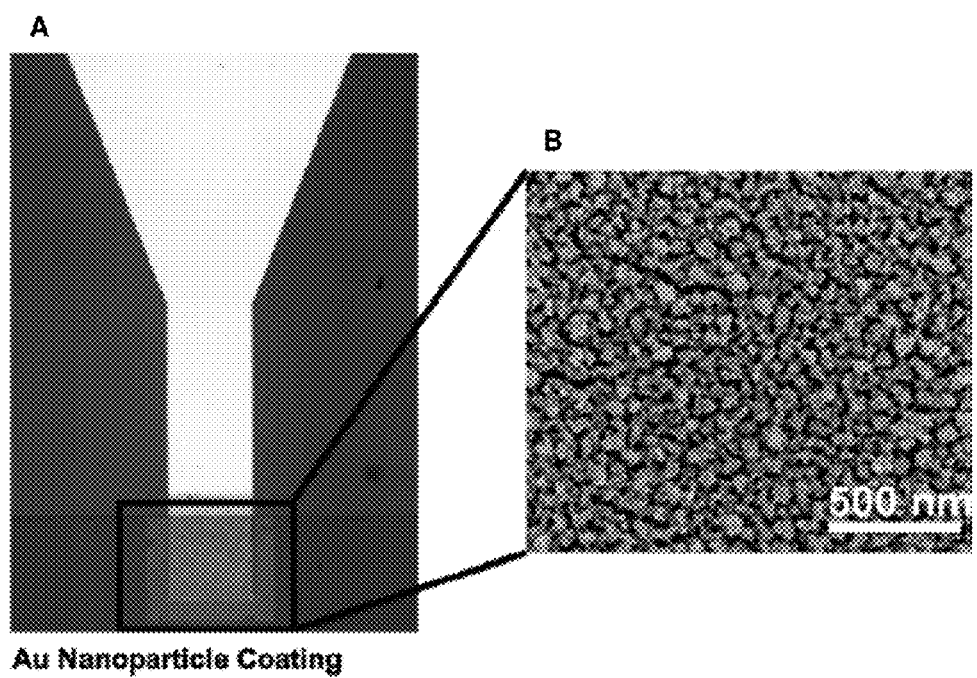

FIGS. 6A-6B: (A) shows a nanocomposite coating comprising gold nanoparticles formed on an implantable component. (B) is an SEM image of such a nanocomposite coating comprising gold nanoparticles (having a scale bar of 500 nm).

FIGS. 7A-7D: EDAX spectra of CNT films (FIGS. 7A, 7C) and Au NPs (FIG. 7B, 7D) LBL films before (FIG. 7A, 7B) and after (FIGS. 7C, 7D) microfabrication on silicon substrates.

Figure 8:
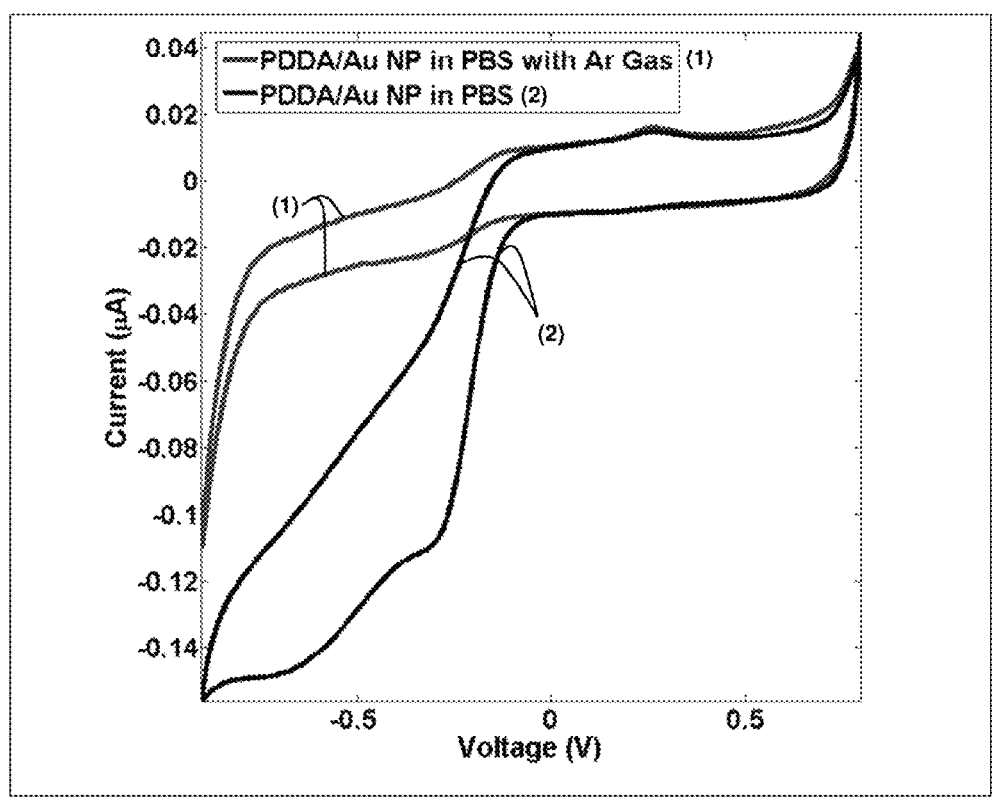

FIG. 8: shows cyclic voltammetry of a nanocomposite comprising gold nanoparticles (Au NP) and PDDA with PBS solution and argon purges with PBS solution.

Figures 9A, 9B:
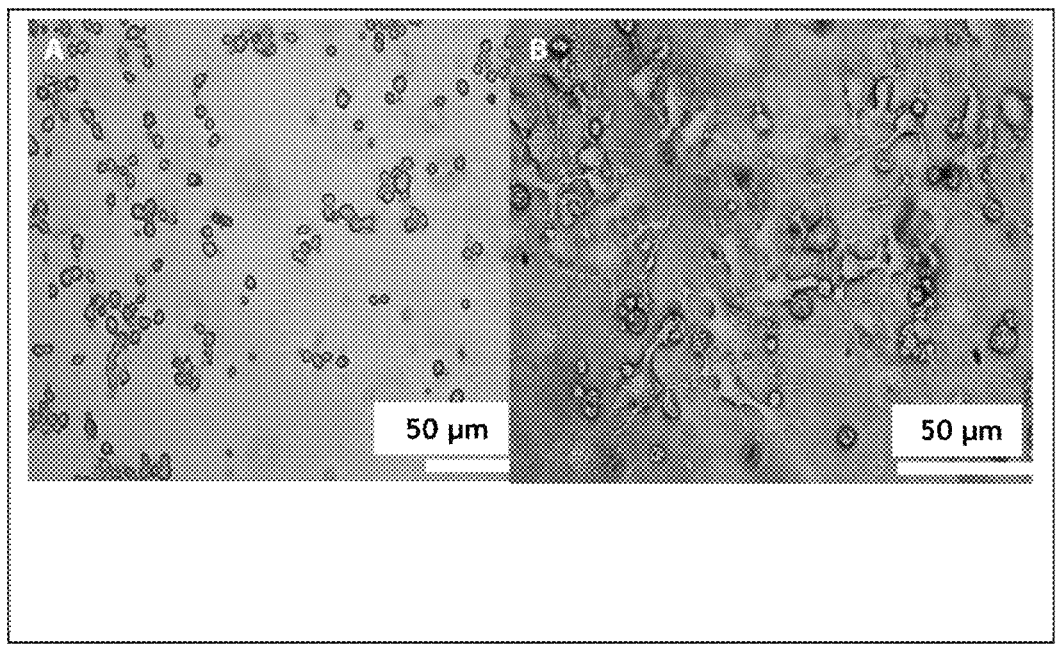

FIGS. 9A-9B: show Optical Images of (A) pre-differentiated NG-108 cells (B) differentiated NG-108 cells on Au NP/PDDA film.

Figures 10A, 10B:
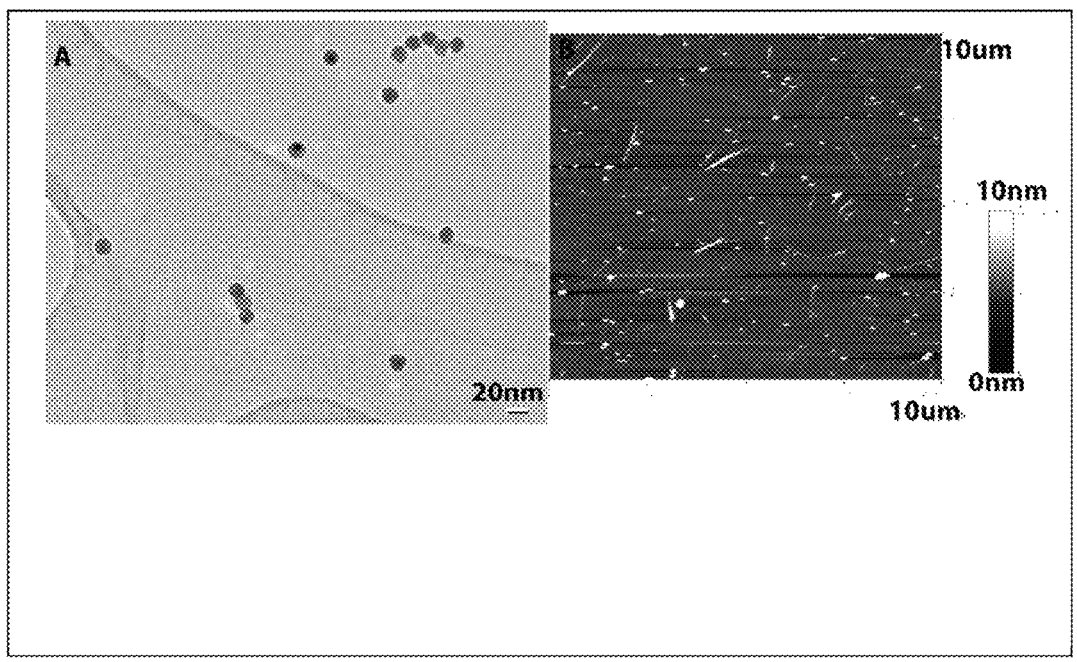

FIGS. 10A-10B: (A) is a TEM image of as synthesized Au NP. (B) is an AFM image of dispersed CNT.

Figures 11A, 11B:
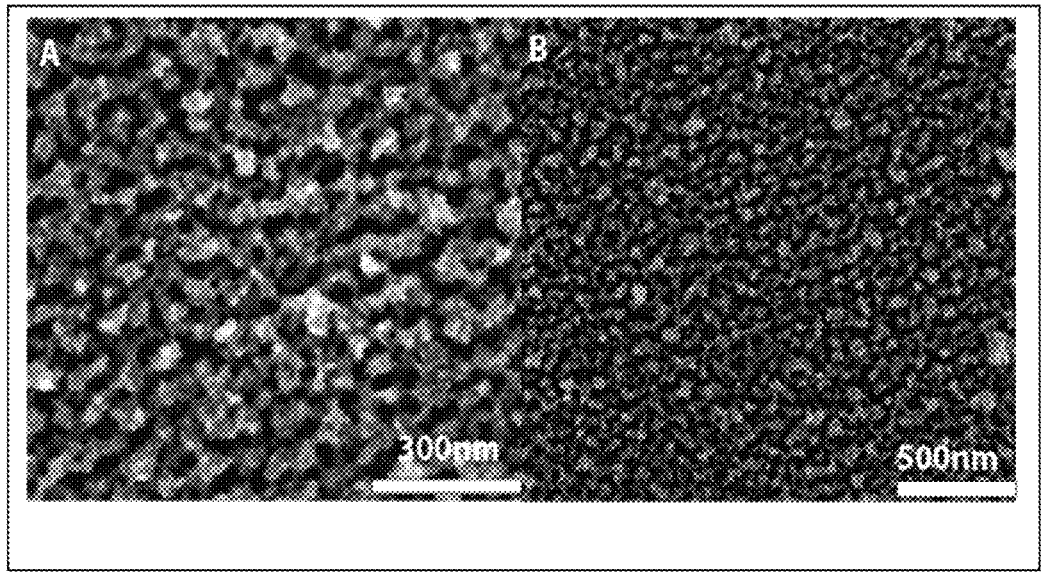

FIGS. 11A-11B: high resolution SEM images of a nanocomposite film comprising gold nanoparticles. (A) has a scale bar of 300 nm and (B) has a scale bar of 500 nm.

Figures 12A, 12B:
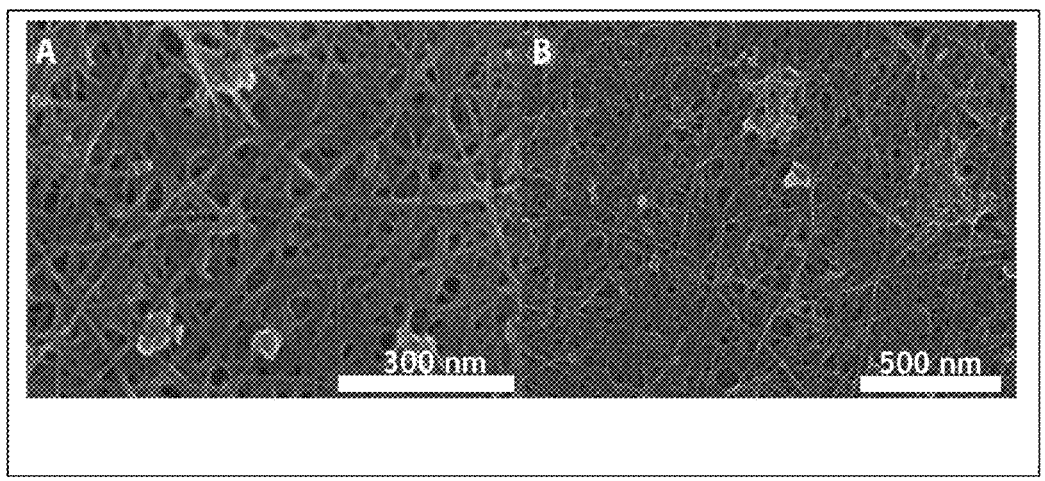

FIGS. 12A-12B: high resolution SEM images of a carbon nanotube containing film. (A) has a scale bar of 300 nm and (B) has a scale bar of 500 nm.

FIGS. 13A-13D: (A) Fabrication scheme for forming a nanocomposite comprising nanoparticles (e.g., carbon nanotubes in a matrix) into an implantable electrode according to certain variations of the present teachings. (B) Optical image of as-made electrodes on glass substrate. (C) SEM image of the 10 µm wide implantable electrode. (D) SEM image of the CNT functional site.

Figure 14A:
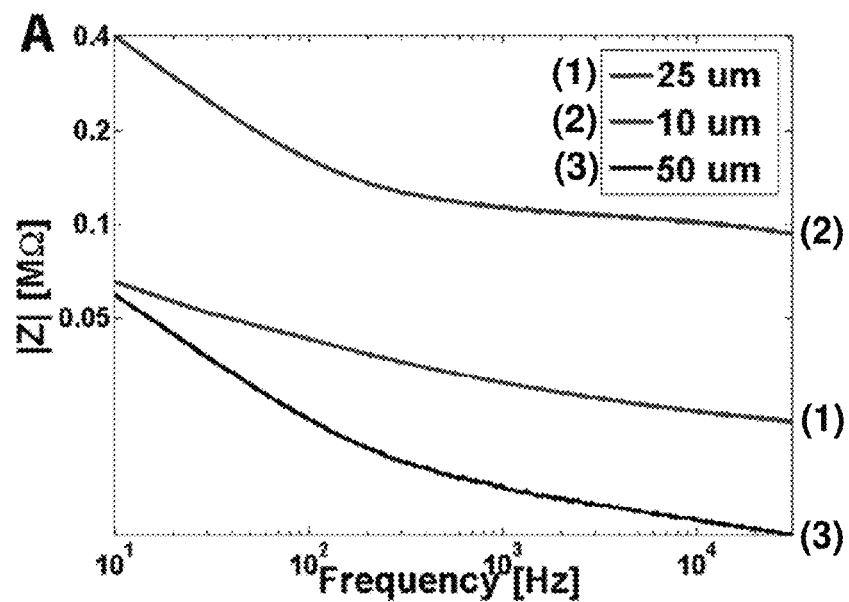
Figure 14B:
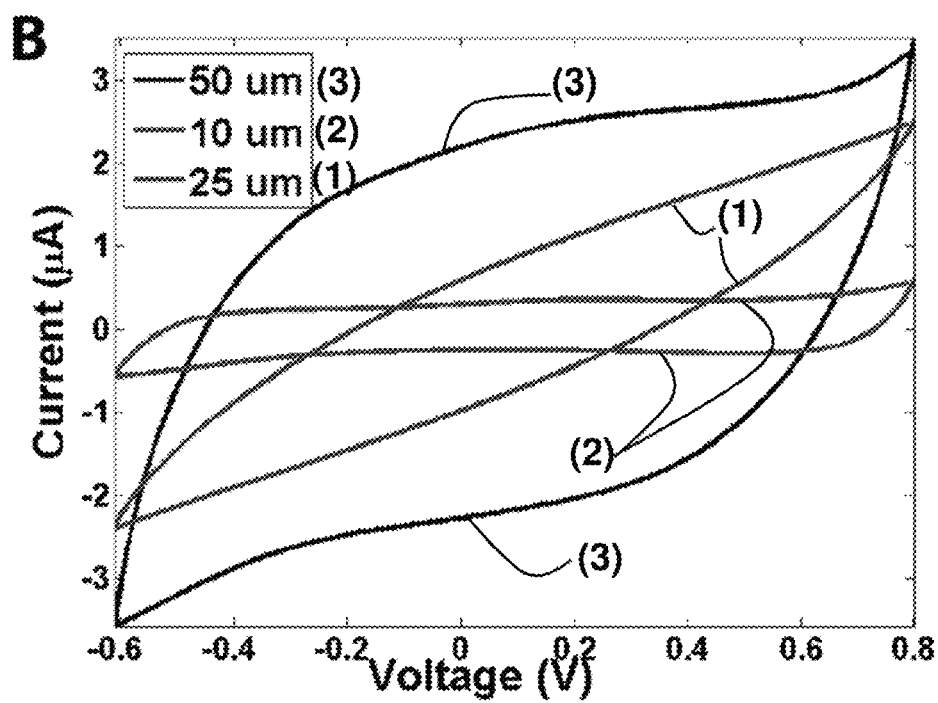
Figure 14C:
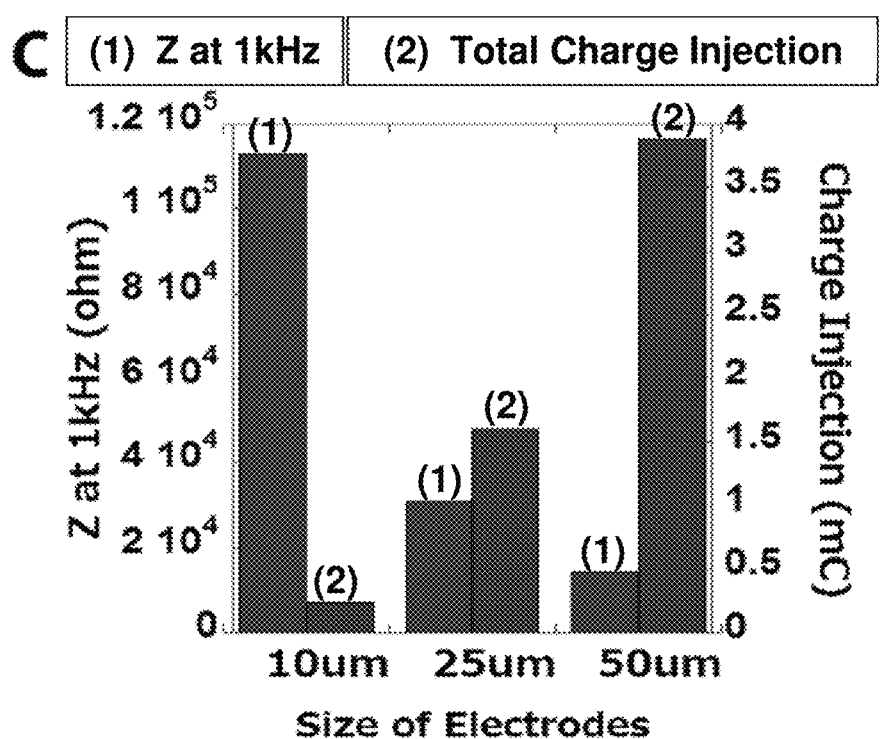

FIGS. 14A-14C show electrochemical characterization of different size electrodes. (A) Frequency dependence of impedance, Z. (B) Cyclic voltammetry from 0.8 V to −0.6 V. (C) Cumulative electrochemical properties of the compliant nanotube electrodes.

FIGS. 15A-15E: (A) Schematic of the photoacoustic microscopy (PAM) setup. (B) PAM image of two electrodes inserted into the brain. (C) Zoomed out MRI image of the y-z plane. (D) MRI image of the y-z plane. (E) MRI image of the x-y plane.

FIGS. 16A-16D: (A) Schematic of a process for preparing an implantable flexible electrode/shuttle assembly. (B) Animal brain after recording experiment. (C) Local field potential recorded from the brain. (D) Power spectrum of the local field potential recording.

Figures 17A, 17B:
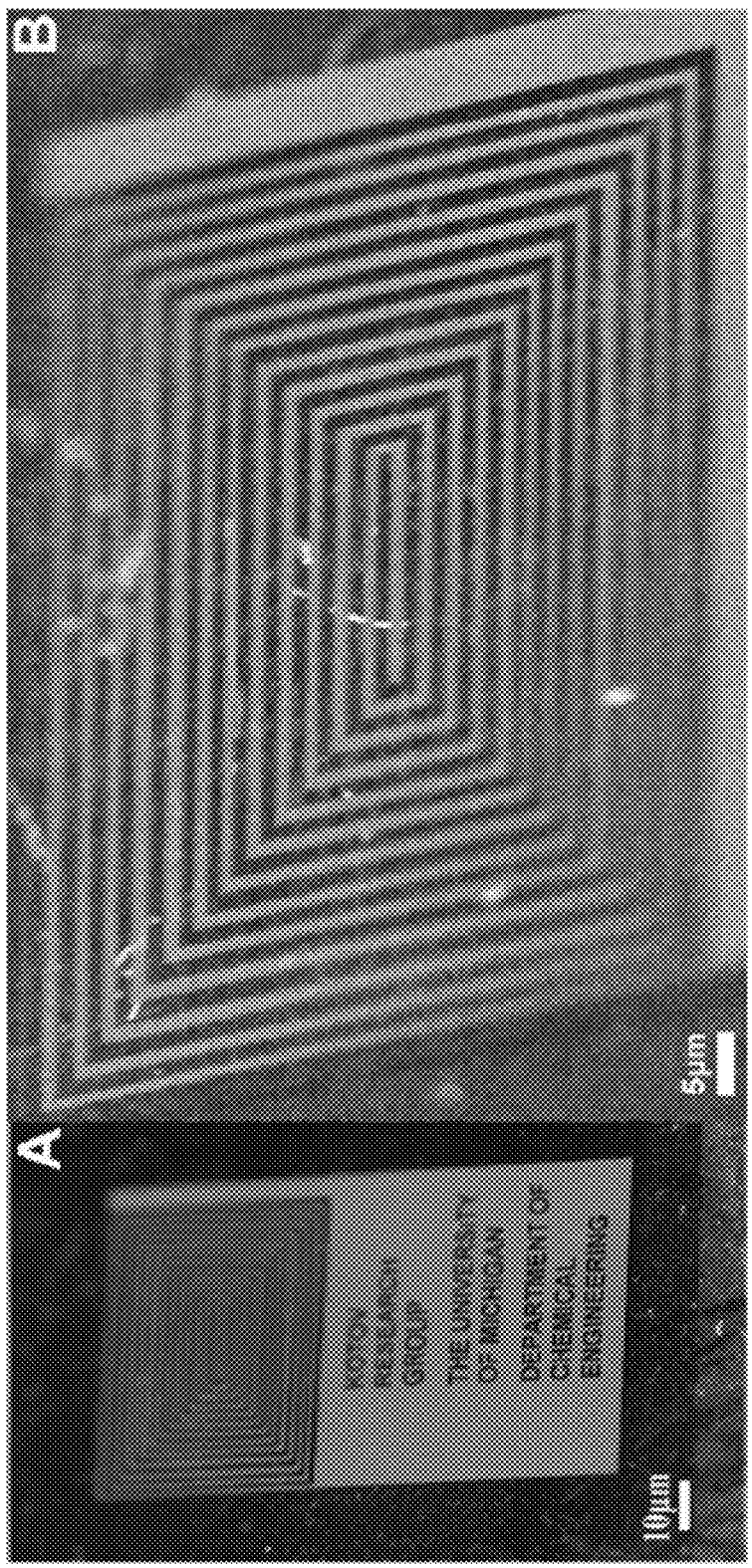

FIGS. 17A-17B: photographs of prototypical spiral pattern formed via certain direct write lithographic techniques in accordance with the present teachings on a nanocomposite comprising single walled nanotubes and chitosan (CH/SWNT)$_{300}$ films. (A) is the as-fabricated pattern before etching. (B) pattern feature after oxygen plasma etching.

Figures 18A, 18B:
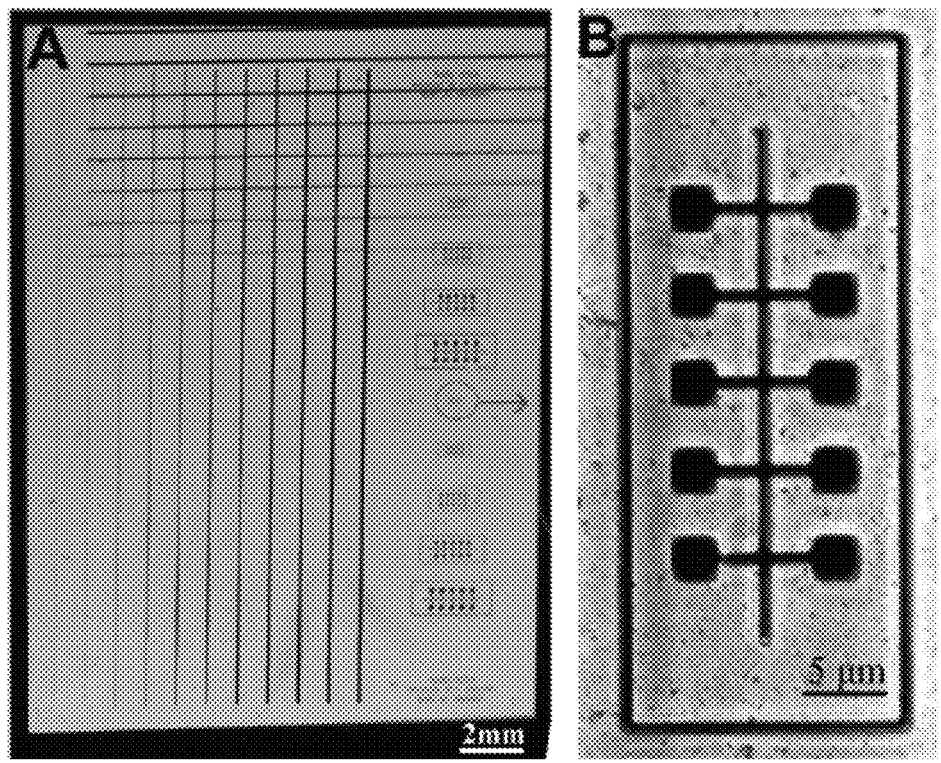

FIGS. 18A-18B: photographs of patterns formed by certain direct write lithographic techniques in accordance with the present teachings on a nanocomposite comprising single walled nanotubes and chitosan (CH/SWNT)$_{500}$ films on a glass substrate. (A) shows an orthogonal linear array. (B) a detailed view of the circled portion of 18A, showing bus-line-and-stimulation-pads (BLASP) patterning.

Figures 19A, 19B, 19C:
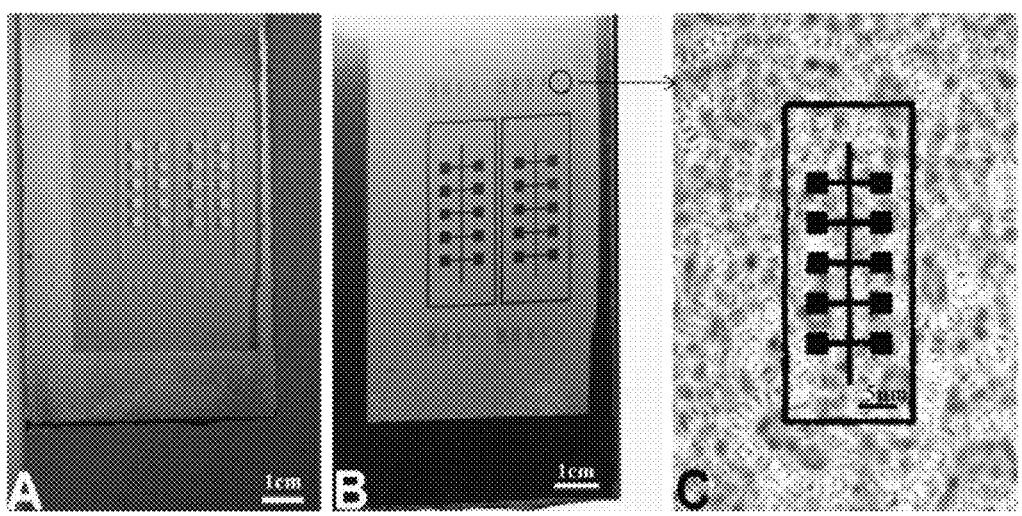

FIGS. 19A-19C: photographs of patterns formed by certain direct write lithographic techniques in accordance with the present teachings on a nanocomposite comprising gold nanoparticles and chitosan (CH/Au NP)$_{50}$ on a substrate. (A, B) are photographs of BLASP patterns with sequentially smaller features made on (CH/Au NP)$_{50}$ films at different illumination angles. (C) a detailed microscale photography image of the circled portion of 19B.

Corresponding reference numerals indicate corresponding parts throughout the several views of the drawings.

DETAILED DESCRIPTION

Example embodiments will now be described more fully with reference to the accompanying drawings.

Example embodiments are provided so that this disclosure will be thorough, and will fully convey the scope to those who are skilled in the art. Numerous specific details are set forth such as examples of specific components, devices, and methods, to provide a thorough understanding of embodiments of the present disclosure. It will be apparent to those skilled in the art that specific details need not be employed, that example embodiments may be embodied in many different forms and that neither should be construed to limit the scope of the disclosure. In some example embodiments, well-known processes, well-known device structures, and well-known technologies are not described in detail.

The terminology used herein is for the purpose of describing particular example embodiments only and is not intended to be limiting. As used herein, the singular forms "a," "an," and "the" may be intended to include the plural forms as well, unless the context clearly indicates otherwise. The terms "comprises," "comprising," "including," and "having," are inclusive and therefore specify the presence of stated features, integers, steps, operations, elements, and/or components, but do not preclude the presence or addition of one or more other features, integers, steps, operations, elements, components, and/or groups thereof. The method steps, processes, and operations described herein are not to be construed as necessarily requiring their performance in the particular order discussed or illustrated, unless specifically identified as an order of performance. It is also to be understood that additional or alternative steps may be employed.

When an element or layer is referred to as being "on," "engaged to," "connected to," or "coupled to" another element or layer, it may be directly on, engaged, connected or coupled to the other element or layer, or intervening elements or layers may be present. In contrast, when an element is referred to as being "directly on," "directly engaged to," "directly connected to," or "directly coupled to" another element or layer, there may be no intervening elements or layers present. Other words used to describe the relationship between elements should be interpreted in a like fashion (e.g., "between" versus "directly between," "adjacent" versus "directly adjacent," etc.). As used herein, the term "and/or" includes any and all combinations of one or more of the associated listed items.

Although the terms first, second, third, etc. may be used herein to describe various elements, components, regions, layers and/or sections, these elements, components, regions, layers and/or sections should not be limited by these terms. These terms may be only used to distinguish one element, component, region, layer or section from another region, layer or section. Terms such as "first," "second," and other numerical terms when used herein do not imply a sequence or order unless clearly indicated by the context. Thus, a first element, component, region, layer or section discussed below could be termed a second element, component, region, layer or section without departing from the teachings of the example embodiments.

Spatially relative terms, such as "inner," "outer," "beneath," "below," "lower," "above," "upper," and the like, may be used herein for ease of description to describe one element or feature's relationship to another element(s) or feature(s) as illustrated in the figures. Spatially relative terms may be intended to encompass different orientations of the device in use or operation in addition to the orientation depicted in the figures. For example, if the device in the figures is turned over, elements described as "below" or "beneath" other elements or features would then be oriented "above" the other elements or features. Thus, the example term "below" can encompass both an orientation of above and below. The device may be otherwise oriented (rotated 90 degrees or at other orientations) and the spatially relative descriptors used herein interpreted accordingly.

Throughout this disclosure, the numerical values represent approximate measures or limits to ranges to encompass minor deviations from the given values and embodiments having about the value mentioned as well as those having exactly the value mentioned. Other than in the working examples provided at the end of the detailed description, all numerical values of parameters (e.g., of quantities or conditions) in this specification, including the appended claims, are to be understood as being modified in all instances by the term "about" whether or not "about" actually appears before the numerical value. "About" indicates that the stated numerical value allows some slight imprecision (with some approach to exactness in the value; approximately or reasonably close to the value; nearly). If the imprecision provided by "about" is not otherwise understood in the art with this ordinary meaning, then "about" as used herein indicates at least variations that may arise from ordinary methods of measuring and using such parameters. In addition, disclosure of ranges includes disclosure of all values and further divided ranges within the entire range, including endpoints given for the ranges.

Neural prosthetic devices (NPDs), such as artificial pacemakers and cochlear implants, are becoming increasingly relevant for the diagnosis and treatment of many neurological conditions and traumas. Commonly, these devices utilize electrodes to interact with neural tissues and achieve targeted stimulation or recording. For example, chronic deep brain stimulation (DBS) can alleviate symptoms of Parkinson's and even Alzheimer's disease. NPDs have also allowed patients of ayomyotrophic lateral sclerosis to regain motor functions. Recently, brain-computer interfaces have received increased attention because of the possibility of using multi-site recording NPD platforms for restoration of mobility and prosthetic devices for limbs. Despite initial clinical successes, there are still many challenges in creating long-lasting, high-performance neural prosthetic devices.

Current neural prosthetic devices induce chronic inflammation due to staggering discrepancies of mechanical properties with neural tissue and relatively large size of the implants. For example, to improve the long-term stability and performance of current NPDs, it is necessary to minimize the inflammatory response induced by NPDs. Typically, after implantation, a layer of scar tissue forms around the NPD due to accumulation of resident immune cells. This layer will create a barrier between the device and the target neural tissue, which causes the device to lose its functionality over time.

Studies have suggested that inflammatory response is substantially reduced as the implant becomes smaller. In certain aspects, the ideal dimensions of implantable neural electrodes are less than or equal to about 10 μm in either width, thickness, or both width and thickness. Moreover, it is demonstrated that subcellular-sized electrodes allow the formation of tight junction between neurons and electrodes, thus creating effective electrical coupling at the neuron/electrode interface. Mechanical properties of the electrodes are also closely related to inflammation. Electrodes made of rigid materials, such as noble metals and semiconductors have large mismatches in mechanical properties with neural tissues. This mismatch becomes particularly significant when considering the inevitable microscale motion of electrodes relative to the brain or other tissues. This motion triggers additional immune response through mechanical signal transduction. Smaller flexible electrodes have better compliance with soft tissues and are believed to help reduce the additional activation of immune reactions and scar formation.

An improved tissue/device interface requires a new generation of neural devices, such as those fabricated from flexible materials exhibiting a combination of both superior mechanical performance and electrical performance, which are not currently available in neurotechnology. In addition to surmounting the fundamental challenges of implantable devices, especially for NPDs, development of such materials is desirably combined with their integration with micromanufacturing techniques and innovative methods of implantation. Despite tremendous activity in the area of neural interfaces with carbon nanotubes (CNTs), fully functioning microdevices fabricated from CNTs have not yet been realized until the present teachings.

While the concept of ultra-small flexible electrodes is well understood, the pathway to its practical realization is not. For example, the ultra-small dimensions of electrodes raise challenging material issues. The electrical properties of all currently available classical and advanced materials, as exemplified by platinum, doped silicon, polypyrrole, poly(3,4-ethylenedioxythiophene) (PEDOT), and iridium oxide (IrOx), greatly limit the functionalities of electrodes smaller than 50-100 μm. Furthermore, the charge storage capacity and interfacial impedance of these materials are not sufficient to reliably record signals from electrodes below this size. Even under the best circumstances, the maximum charge injection of noble metal neural electrodes with 200 μm$^2$ functional site is 0.0003 μC, which is well below a typical charge of 0.2 to 0.5 μC; thus there are tradeoffs in miniaturizing functional sites and electrode sizes.

The inventive technology provides new materials with improved interfacial impedance (Z) and charge storage capacity (CSC) as compared to currently available conventional materials. Lower electrical impedance improves signal-to-noise ratio and the long-term recording quality of NPDs and reduces harmful over potential. High CSC materials can deliver a higher charge per area of the electrodes to the surrounding tissue for neural stimulation. The general strategy for improving Z and CSC is to increase the electrochemical surface area of the electrodes for a given geometric surface area. Most advanced currently available materials used for neural electrodes, including platinum black, conductive polymer, and iridium oxide have high-roughness surfaces to increase the ratio of electrochemical surface area and geometric surface area, consequently improving the Z and CSC.

In various aspects, such an implantable electrically conductive device in accordance with the present teachings comprises an implantable region that comprises a nanocomposite material. In various aspects, the present disclosure provides an implantable electrically conductive device comprising a nanocomposite material disposed on or forming an implantable region of an implantable component. The nanocomposite material comprises a plurality of nanoparticles selected from the group consisting of: gold nanoparticles, carbon nanotubes, and combinations thereof. In various aspects, the implantable region of the implantable electrically conductive device is electrically conductive and flexible. Flexible materials are capable of significant elongation, flexing, bending or other deformation along one or more axes. The term "flexible" can refer to the ability of a material, structure, or component to be deformed (for example, into a curved shape) without undergoing a permanent transformation that introduces significant strain, such as strain indicating a failure point of a material, structure, or component.

The nanocomposite material comprises a matrix material, such as a polymer or a polyelectrolyte. The nanocomposite also comprises a plurality of electrically conductive nanoparticles. "Nanocomposite" in intended to mean a composite material that comprises nanoparticles. A "nanoparticle" is a solid or semi-solid material that can have a variety of shapes or morphologies, however, which are generally understood by those of skill in the art to mean that the particle has at least one spatial dimension that is less than or equal to about 10 μm (10,000 nm). In certain aspects, a nanoparticle has a relatively low aspect ratio (AR) (defined as a length of the longest axis divided by diameter of the component) of less than or equal to about 100, optionally less than or equal to about 50, optionally less than or equal to about 25, optionally less than or equal to about 20, optionally less than or equal to about 15, optionally less than or equal to about 10, optionally less than or equal to about 5, and in certain variations, equal to about 1. In other aspects, a nanoparticle that has a tube or fiber shape has a relatively high aspect ratio (AR) of greater than or equal to about 100, optionally greater than or equal to about 1,000, and in certain variations, optionally greater than or equal to about 10,000.

In certain preferred variations, a nanoparticle's longest dimension is less than or equal to about 100 nm. In certain aspects, a nano-particle has at least one spatial dimension that is greater than or equal to about 10 nm and less than or equal to about 100 nm. In certain embodiments, the nanoparticles selected for inclusion in the electrically conductive nanocomposite material comprise substantially round-shaped nanoparticles. "Substantially round-shaped" includes nanoparticles having low aspect ratios as defined above and also having a morphology or shape including spherical, spheroidal, hemispherical, disk, globular, annular, toroidal, cylindrical, discoid, domical, egg-shaped, elliptical, orbed, oval, and the like. In certain preferred variations, the morphology of the nanoparticle has a spherical shape. In certain alternative variations, the nanoparticle may have an alternative shape, such as a nanostar or a nanoshell. In other variations, the nanoparticle may be a filament, fiber, rod, or a nanotube.

Furthermore, in certain aspects, a particularly suitable nanoparticle for use in accordance with the present teachings has a particle size (an average diameter for the plurality of nanoparticles present) of greater than or equal to about 10 nm to less than or equal to about 100 nm. In certain variations, the nanoparticle has an average particle size diameter of greater than or equal to about 5 nm to less than or equal to about 50 nm; optionally greater than or equal to about 10 nm to less than or equal to about 50 nm, and in certain variations, optionally greater than or equal to about 10 nm to less than or equal to about 30 nm. The conductive nanoparticles may be formed of a variety of conductive materials including metallic and semiconducting nanoscale particles. The nanoparticles are preferably biocompatible and may comprise gold or graphite/graphene or other similar materials known to those of skill in the art. In certain preferred variations; however, the nanoparticles comprise gold. In other alternative variations, the nanoparticles can comprise carbon nanotubes, such as single walled nanotubes (SWNTs) or multi-walled nanotubes (MWNTs), for example. Single-walled carbon nanotubes (SWNT) are formed from a single sheet of graphite or graphene, while multi-walled carbon nanotubes (MWNT) consist of multiple cylinders arranged in a concentric fashion. The typical diameters of SWNT can range from about 0.8 nm to about 2 nm, while MWNT can have diameters in excess of 100 nm.

The inventive implantable electrically conductive devices comprise soft and flexible implantable components, e.g., neural electrodes that reduce mechanical mismatch. In certain variations, the plurality of nanoparticles comprise gold. In certain other alternative variations, the plurality of nanoparticles comprises carbon nanotubes. The nanocomposite material may thus be formed as a coating on the implantable component. In certain variations, such as where the plurality of nanoparticles are gold nanoparticles, the nanocomposite material may preferably be disposed (e.g., as a thin film or coating) on an implantable region of an implantable component formed of a distinct material, for example. The nanocomposite material may be used as a structural material to form an implantable region of the implantable component. In certain variations, such as where the plurality of nanoparticles is carbon nanotubes, the nanocomposite material may preferably form the structure of the implantable region of the implantable component.

In certain aspects, the implantable region of the implantable electrically conductive device has at least one dimension less than or equal to about 25 micrometers (μm), optionally less than or equal to about 20 μm, optionally less than or equal to about 15 μm, and in certain preferred aspects, at least one dimension that is optionally less than or equal to about 10 μm. It should be noted that so long as at least one dimension of the implantable electrically conductive device falls within the above-described dimension, (e.g., diameter or width), one or more other axes or dimensions may well exceed this dimension (e.g., length). In certain variations, the implantable region of the implantable electrically conductive device has at least two physical dimensions comparable to that of cells (approximately 10 µm), which can further and substantially reduce chronic inflammation. Thus, in certain other variations, the implantable electrically conductive device has an implantable region that has a first dimension that is less than or equal to about 25 micrometers (µm), optionally less than or equal to about 20 µm, optionally less than or equal to about 15 µm, and in certain aspects, a first dimension that is less than or equal to about 10 µm, while also having a second distinct dimension that is less than or equal to about 50 µm, optionally less than or equal to about 40 µm, optionally less than or equal to about 30 µm, optionally less than or equal to about 25 µm, optionally less than or equal to about 20 µm, optionally less than or equal to about 15 µm, and in certain preferred aspects, the second dimension is optionally less than or equal to about 10 µm.

Thus, in certain variations, where the electrically conductive nanocomposite is a biocompatible film or coating, it optionally has a thickness of less than 1 µm, optionally less than or equal to about 500 nm, optionally less than or equal to about 400 nm, optionally less than or equal to about 300 nm, optionally less than or equal to about 200 nm, optionally less than or equal to about 150 nm, optionally less than or equal to about 100 nm, optionally less than or equal to about 50 nm, optionally less than or equal to about 25 nm, optionally less than or equal to about 20 nm, optionally less than or equal to about 15 nm, and optionally less than or equal to about 10 nm.

In certain variations, an electrical conductivity of the electrically conductive nanocomposite comprising a plurality of nanoparticles is greater than or equal to about $1.5 \times 10^3$ S/cm. In certain aspects, the implantable region of the implantable electrically conductive device has an electrical conductivity of greater than or equal to about $1 \times 10^5$ S/cm, optionally greater than or equal to about $1.1 \times 10^5$ S/cm, optionally greater than or equal to about $1 \times 10^6$ S/cm, optionally greater than or equal to about $2 \times 10^6$ S/cm, optionally greater than or equal to about $3 \times 10^6$ S/cm, optionally greater than or equal to about $4 \times 10^6$ S/cm, optionally greater than or equal to about $5 \times 10^6$ S/cm, optionally greater than or equal to about $6 \times 10^6$ S/cm, optionally greater than or equal to about $7 \times 10^6$ S/cm, optionally greater than or equal to about $8 \times 10^6$ S/cm, and in certain variations, optionally greater than or equal to about $8.6 \times 10^6$ S/cm.

In certain other aspects, the implantable region of the implantable electrically conductive device may have an electrical resistivity of less than or equal to about $1 \times 10^{-4}$ Ohm·m, optionally less than or equal to about $9 \times 10^{-5}$ Ohm·m, optionally less than or equal to about $8 \times 10^{-5}$ Ohm·m, optionally less than or equal to about $7 \times 10^{-5}$ Ohm·m, optionally less than or equal to about $6 \times 10^{-5}$ Ohm·m, optionally less than or equal to about $5 \times 10^{-5}$ Ohm·m, optionally less than or equal to about $4 \times 10^{-5}$ Ohm·m, optionally less than or equal to about $3 \times 10^{-5}$ Ohm·m, optionally less than or equal to about $2 \times 10^{-5}$ Ohm·m, optionally less than or equal to about $1 \times 10^{-5}$ Ohm·m, optionally less than or equal to about $9 \times 10^{-6}$ Ohm·m, optionally less than or equal to about $8 \times 10^{-6}$ Ohm·m, optionally less than or equal to about $7 \times 10^{-6}$ Ohm·m, optionally less than or equal to about $6 \times 10^{-6}$ Ohm·m, optionally less than or equal to about $5 \times 10^{-6}$ Ohm·m, optionally less than or equal to about $4 \times 10^{-6}$ Ohm·m, optionally less than or equal to about $3 \times 10^{-6}$ Ohm·m, optionally less than or equal to about $2 \times 10^{-6}$ Ohm·m, and in certain embodiments, optionally less than or equal to about $1 \times 10^{-6}$ Ohm·m.

In certain other variations, an impedance (Z) of the electrically conductive nanocomposite comprising a plurality of nanoparticles may be less than or equal to about $1 \times 10^4$ Ohms (e.g., measured using an AC sinusoidal signal of 25 mV in amplitude with impedance values measured at a frequency of 1 kHz), optionally less than or equal to about $9 \times 10^3$ Ohms, optionally less than or equal to about $7 \times 10^3$ Ohms, optionally less than or equal to about $5 \times 10^3$ Ohms, optionally less than or equal to about $3 \times 10^3$ Ohms. In certain variations, such impedance (Z) of an electrically conductive nanocomposite may be less than or equal to about $1 \times 10^3$ Ohms, optionally less than or equal to about $9 \times 10^2$ Ohms, optionally less than or equal to about $7 \times 10^2$ Ohms, optionally less than or equal to about $5 \times 10^2$ Ohms, optionally less than or equal to about $3 \times 10^2$ Ohms, optionally less than or equal to about $2 \times 10^2$ Ohms, and in certain variations optionally less than or equal to about $1 \times 10^2$ Ohms.

In certain aspects, the implantable region of the implantable device may have a charge storage capacity (CSC) of greater than or equal to about 5 mC/cm$^2$ (e.g., at a scan rate of 0.1 V/s from −0.9 to 0.5 V), optionally greater than or equal to about 6 mC/cm$^2$, optionally greater than or equal to about 7 mC/cm$^2$, optionally greater than or equal to about 8 mC/cm$^2$, optionally greater than or equal to about 9 mC/cm$^2$, and in certain variations, optionally greater than or equal to about 10 mC/cm$^2$.

In certain variations, the nanocomposite may comprise a total amount of a plurality of nanoparticles of greater than or equal to about 1% by weight to less than or equal to about 97% by weight, optionally greater than or equal to about 3% by weight to less than or equal to about 95% by weight, optionally greater than or equal to about 5% by weight to less than or equal to about 75% by weight, optionally greater than or equal to about 7% by weight to less than or equal to about 60% by weight, optionally greater than or equal to about 10% by weight to less than or equal to about 50% by weight of a total amount of nanoparticles in the nanocomposite. Of course, appropriate amounts of nanoparticles in a composite material depend upon material properties, percolation thresholds, and other parameters for a particular type of nanoparticle in a specific matrix material.

In certain variations, the nanocomposite may comprise a total amount of a matrix material of greater than or equal to about 1% by weight to less than or equal to about 97% by weight, optionally greater than or equal to about 10% by weight to less than or equal to about 95% by weight, optionally greater than or equal to about 15% by weight to less than or equal to about 90% by weight, optionally greater than or equal to about 25% by weight to less than or equal to about 85% by weight, optionally greater than or equal to about 35% by weight to less than or equal to about 75% by weight, optionally greater than or equal to about 40% by weight to less than or equal to about 70% by weight of a total amount of matrix material in the nanocomposite.

The implantable electrically conductive device may be sized according to the size of the cells, tissue, and/or patient's organ in which it is to be implanted. The present disclosure contemplates using implantable electrically conductive devices independently implanted within target tissue or a target organ of a patient or alternately being used in conjunction with or coupled to medical devices or other types of medical implants, known to those of skill in the art, which are introduced and/or implanted internally in the patient. For example, to monitor the brain, a neural probe can be directly implanted through a burr hole in the skull of the patient. By way of another non-limiting example, the implantable electrically conductive device can be a microelectrode used in a cardiac pacemaker, monitoring assemblies, in/around peripheral nerves or a spine, under the skin, or in stents implanted in heart tissue or vasculature.

In various aspects, the inventive technology provides an implantable region of an implantable electrically conductive device that is relatively strong so that the micro-component is capable of being incorporated into a device that can be implanted in vivo and is relatively flexible to reduce potential stress at an interface with surrounding tissue to mitigate cellular damage adjacent to the implantable device. Electrically conductive nanocomposites incorporated into implantable devices, for example, as microelectrodes, can be used for electrophysiological recordings as well as recording the changes in concentration level of neural chemicals in the brain or in the body. In other embodiments, electrically conductive nanocomposites incorporated into implantable devices, such as microelectrodes, may conduct electrical current or potential from an external source, for example, as a probe or in a cardiac pace-maker application. Devices incorporating such nanocomposites create long-lasting, high-fidelity neural interfaces, which may optionally further have biomimetic materials and surfaces. In certain variations, such electrically conductive implantable devices are incorporated into advanced implantable neural probes for long-term (permanent), high quality and selective neural recording.

In certain aspects, conductive nanomaterials are believed to be ideal for engineering the surfaces of the neural electrodes. CNTs have conventionally been considered a better choice for such neural interface applications due to their fibrous morphology, high electron mobility, and high surface area. For example, CNT-based coatings improve in vivo neural recording in both rats and primates. Despite excellent mechanical properties of CNTs, the electrochemical performance of conventional CNT composites used as coatings on other materials is still not as high as needed for ultrasmall NPD devices, for example, for implantable devices having dimensions of less than or equal to about 10 µm.

Nanoporous gold and gold nanopowder have been considered for neural interface applications as pure materials to form the implantable device. Studies have demonstrated the possibility of creating high roughness gold surfaces. However, these techniques require extensive instrumentation (ultrahigh vacuum deposition and mold fabrication) and high-processing temperatures.

In certain variations, the present disclosure provides an implantable region of an implantable electrically conductive device that includes a conductive nanomaterial. A nanocomposite comprises a plurality of nanoparticles, such as gold nanoparticles, disposed or dispersed in a matrix material, such as a polymer or polyelectrolyte. The nanocomposite material is biocompatible and capable of exhibiting high mechanical flexibility, while also having the desired dimensions and electrochemical performance to serve as an implantable electrode that desirably can avoid inflammation and rejection of the device when implanted in tissue or in an organism.

In certain aspects, the present disclosure provides gold nanoparticle nanocomposites that can successfully be employed in functional electrodes, like implantable neural prosthetic devices. Thus, in certain variations, the present disclosure provides solution-processed gold nanoparticles (Au NPs) for use as a material in an implantable device, like an electrode. Au NPs have minimal toxicity, are highly conductive, and are relatively easy to fabricate. Au NP/polymer composites incorporating the Au NPs have good electrochemical performance and biocompatibility, which are especially well suited for neural interface applications.

In other variations that will be discussed further below, the electrochemical performance of conventional CNT composites has been improved to be as high as desired for ultrasmall NPD devices. For example, in certain aspects, the implantable region of the device, in other words, the structural component itself that is implanted, may be formed entirely of the nanocomposite comprising the carbon nanotubes, rather than coated with a nanocomposite layer, which serves to improve the electrochemical performance. Hence, in certain variations, the present disclosure provides nanocomposites comprising carbon nanotubes that can successfully be employed in functional electrodes, like implantable neural prosthetic devices.

In accordance with certain aspects of the present teachings, composite materials comprising solution-processed gold nanoparticles are capable of better electrochemical performance than composites comprising CNTs. However, in certain alternative variations, the present teachings also contemplate implantable electrically conductive devices that comprise a nanocomposite comprising a plurality of conductive nanoparticles that comprises carbon nanotubes. In certain aspects, a nanocomposite that comprises a plurality of gold particles may exhibit better electrochemical performance than a variation comprising a plurality of carbon nanotubes, however, in certain applications, the carbon nanotubes provide desired mechanical flexibility as a trade-off for relatively less electrochemical performance. Measurements of electrochemical properties on NPD prototypes indicate that with respect to Z and CSC, the Au NP films prepared in accordance with certain aspects of the present technology substantially outperform single wall nanotube (SWNT) composite films with regard to electrochemical performance. Because the microfabrication process developed here for Au NP or CNT nanocomposites is compatible with current microelectrode technology, the present teachings contemplate a new generation of implantable electrodes employing a variety of nanoparticles.

In accordance with certain aspects of the present teachings, a deposition technique can be used called layer-by-layer assembly (LBL) that provides a reliable method for fabricating nanocomposites comprising a plurality of nanoparticles having desired characteristics. The principle of the LBL technique relies on alternating adsorption of polyelectrolytes onto a substrate. The layers are built up by sequential dipping of the substrate into oppositely charged polyelectrolyte solutions. Monolayers of individual components attracted to each other by electrostatic and van-der-Waals interactions are sequentially adsorbed on the substrate.

In certain embodiments, the present disclosure provides method for forming such nanocomposites via a layer-by-layer assembly. A first layer comprising at least one nanoparticle species, like gold nanoparticles or carbon nanotubes, is formed. A layer is generally believed to be formed by the electrostatic self-assembly of a single layer of an organic or polymer molecule followed by a layer of particles in a layer-by-layer fashion at room temperature. The combination of nanoscale particles and flexible polymer molecules makes it possible to fabricate composite films. Thus, a plurality of layers may be formed sequentially to form a desired composite. The layer-by-layer composites formed in this manner comprise one or more nanoparticles. Such nanoparticles may optionally have an average particle size diameter of less than or equal to about 1 µm, optionally of less than or equal to about 500 nm, optionally of less than or equal to about 100 nm, and in certain aspects, optionally less than or equal to about 50 nm.

The process of forming a composite material comprising nanoparticles (e.g., Au NPs or CNTs) by a layer-by-layer technique may comprise: 1) providing a substrate; 2) optionally modifying the substrate to impart a charge; 3) contacting the substrate with a polyelectrolyte (e.g., by spraying, dipping, or coating); 4) rinsing the substrate with cleansing solution; 5) contacting the substrate with a suspension or solution comprising the nanoparticles, so that the nanoparticles overlie the polyelectrolyte on the target substrate; 6) rinsing the substrate with cleansing solution; and 7) repeating the steps of 3) to 6) to yield a multilayer coated substrate that ultimately forms a nanocomposite material.

In certain embodiments, where the nanocomposite is disposed on an implantable component, such as a coating on an electrode or other implantable device, a support substrate is may be used that is formed of a biologically compatible material that can be electrically conducting or semi-conducting, for example. See, for example, FIG. 6A showing an exemplary implantable device having a nanocomposite comprising gold nanoparticles formed as a coating on a terminal region of the device. The inset in FIG. 6B shows an SEM image of the same gold nanoparticle coating on the substrate at the terminal region of the device. Such biologically compatible substrate materials are well known in the art. The chemical nature of these substrates can be inorganic or organic. In certain variations, the implantable material or substrate may be formed of a conductive material, although this is not necessary, as the nanocomposite comprising gold nanoparticles is itself electrically conductive. Non-limiting examples of inorganic support or substrate materials include by way of non-limiting example, metals, such as gold or platinum, and semi-conductor materials, such as glasses or ceramic materials. Organic materials for the support or substrate materials can be selected to be polymer materials or carbon-containing materials, like graphite, by way of non-limiting example.

The matrix materials may be polymers or polyelectrolytes. In certain variations, the polymers or polyelectrolytes can be any ionic solution capable of forming a layer on a surface of a substrate, depending on the deposition or layering method. Again, biologically compatible materials are desirable for selection as the polyelectrolyte. In certain embodiments, the polyelectrolyte can be any charged species, including without limitation, poly(diallydimethylammonium chloride) (PDDA), chitosan (CH), poly(styrene sulfonate) (PSS), poly (vinyl alcohol), aluminosilicate clay (montmorillonite), ionic polymers, for example, polylysine, oligonucleotides, polyacetylamine, collagen, alginate, carageenan, fibronectin, gelatin, extra-cellular matrix, poly(ethyleneimine) (PEI), poly(allylamine hydrochloride (PAH), poly aniline, polyacrylic acid, polylactic acid, and compositions containing cellulose, for example.

CNT composites have been shown to have superior electrical and mechanical properties upon cyclic excitation, as compared to conventional IrOx and PEDOT materials. The conductivity of macroscale composite materials made from Au NPs according to various aspects of the present disclosure is believed to be higher than any conventional CNT composites. While the charge transport in a single carbon nanotube can be exceptionally fast, this does not mean that it is possible to translate it to macroscale materials. Unfortunately, the insulating gaps between the nanotubes and the Schottky barrier at the interfaces between the semiconductor and metallic nanotubes can potentially frustrate the electron transport in CNT composite materials in macro-scale and micro-scale. Besides high conductivity of macroscale composites, Au NPs provide exceptionally high surface area, which can potentially reduce Z. In various aspects, designs balance the surface area with the interconnectivity of Au NPs. Notably, as discussed further below, in certain variations, the present teachings have addressed certain issues with CNT composite materials used as coatings, by instead forming structural components of the nanocomposite material itself.

Thus, in various aspects, the present disclosure provides new materials that can form functional electrodes, while avoiding the aforementioned issues. In various aspects, the present disclosure provides gold nanoparticle nanocomposites that can successfully be employed in such functional electrodes, like implantable neural prosthetic devices. At certain levels, Au NPs do not appear to interfere with tissue function even after many years of residence time, which is a substantial advantage for use in NPD implants. As such, various nanocomposites according to the present disclosure can be used in tissue-mimetic electrodes for long-term brain-machine interface.

In various aspects, the present teachings provide materials comprising gold nanoparticles, such as gold nanoparticle nanocomposites. Layer-by-layer assembled films comprising Au NPs provide more than three-fold improvement in interfacial impedance and one order of magnitude increase in charge storage capacity. In certain variations, microelectrodes can be made using traditional photolithography. Integration of unique nanocomposite materials with microfabrication techniques of the present teachings opens the door for practical realization of the ultra-small implantable electrodes. Furthermore, it is expected that electrical properties will be further improved when using pre-selected shapes of gold nanoparticles.

In certain alternative embodiments, an electrically conductive implantable device comprises a nanocomposite having a plurality of nanotubes. Carbon nanotubes (CNTs) have exceptional material properties for neural interfaces in terms of electrochemical performance, chemical stability, and mechanical properties. Various studies have looked at CNT coatings formed over traditional electrodes or on silicon substrates. The problem with the mismatch of mechanical properties and corresponding inflammation therefore still persists in such embodiments. Certain issues with using CNT coatings can also be exemplified by CNT layers on polymer substrates. Typically, CNT layers are grown on polymer substrates by using low-temperature growth, as well as stamping techniques. The potential problems include weak adhesion between CNT and substrates that can lead to delamination and fracture during device implantation, and reduced electrical conductivity of low-temperature growth of CNT. Thus, only large dimension electrodes (on 100 μm scale) have been fabricated by these techniques, and their functionality has only been demonstrated on fish nerves in ex vivo experiments.

However, in accordance with the present teachings, layer-by-layer (LBL) assembly of CNT or Au NP nanocomposites may be an alternative to the preparation of composite electrodes that allow for careful engineering of the material and its qualities for tissue-mimicking implants. Layer-by-layer assembly (LBL) is one of the most suitable techniques to impart different properties to thin films and membranes, including the ability to produce coatings and free-standing films on two-dimensional (2D) and three-dimensional (3D) surfaces and topologies at nano-, micro, meso-, and macroscale. LBL composites have also shown unusually high loadings of SWNTs or metal nanoparticles, like gold, to enable engineering of polymer-based interface, and excellent homogeneity of the resulting material.

Thus, the LBL process allows for fine-tuning of the composite structure to achieve optimal mechanical and electrochemical properties. Furthermore, forming such a nanocomposite material enables an implantable region of an implantable component to define a structural body formed from the LBL CNT nanocomposite, rather than merely being a coating over another distinct material. LBL-assembled CNT/polymer composites are often very strong, yet exceptionally flexible, and display the highest conductivity among similar materials. The LBL-assembled CNT nanocomposites prepared in accordance with the present disclosure also outperform the leading advanced materials for neural interface application.

In other aspects, methods of patterning nanocomposites comprising gold nanoparticles or carbon nanotubes (e.g., gold nanoparticle films) are provided. For example, in certain aspects, methods of direct-write maskless lithography of layer-by-layer nanocomposite films are provided. Lithography is used in many areas of modern science and technology, including the production of integrated circuits, microelectromechanical systems (MEMS), flexible displays, information storage devices, printed transistor circuits, miniaturized chemical sensors, microfluidic devices, biochips, photonic band gap structures, and diffractive optical elements. With a few exceptions, lithographic patterns are made from traditional materials: metals, plastics, and semiconductors. While integration of nanoscale materials, such as carbon nanotubes, graphene, and others with lithographic patterning has been successful, the same has not been true for nanocomposites.

Despite unique performance characteristics, conventional methods of nanocomposite synthesis are not easily integrated in the established lithographic processes. At the same time, their ability to combine different and often difficult or impossible to achieve features when using traditional materials can resolve a number of problems of MEMS and other microscale devices. For instance, for microelectronic devices, it may be desirable to employ the inventive composite materials having exceptional mechanical and electrical properties, particularly for stretchable and flexible electronics. MEMS applications will benefit from substantial expansion of palette of magnetic, optical properties, with mechanical toughness necessary for microactuators by the inventive technology. As noted above, biomedical implants are also contemplated as benefitting from the above-mentioned functional properties of such nanocomposites, while also having biocompatibility. Thus, application of nanocomposites like those comprising gold nanoparticles or carbon nanotubes can be used in MEMS, flexible electronics, and/or biomedical devices. Certain methods provided by the present disclosure for making these materials enable new performance standards and resolve a number of difficult technical problems enabled by the unique combinations of electrical, optical, and mechanical properties.

In various aspects, such techniques make microscale nanocomposite patterns using the fusion of two highly versatile techniques: direct-write maskless UV patterning and layer-by-layer assembly (LBL). Together these methods can be applied to production of a wide variety of nanostructured coatings with complex patterns. Conventional methods of fabrication of different patterns from LBL films present challenges with their universality, ability to create complex geometries (bridges, helices, channels and the like), and practicality of such patterns in demanding real-life conditions still remain. As such, none of the described methods demonstrates patterning of composite materials with high performance mechanical materials combined with equally unique electrical properties. In accordance with certain aspects of the present disclosure, a versatile lithographic process applicable to high-performance flexible LBL composite films from single-walled carbon nanotubes or gold nanoparticles (Au NPs) is provided. Well-defined high-resolution microscale patterns are fabricated through state-of-the-art direct-write lithography. Besides other advantages, this type of lithography is one of the simplest methods to make complex microscale patterns, which is successfully realized for the LBL films. These patterns can be used for flexible transistors, sensing elements, integrated circuits, antennas, biomedical implants, and other devices.

Mask-less lithography employed in such variations utilizes tightly focused and collimated UV-laser beam to directly "write" the pattern into the photoresist. This technique is remarkable in its versatility and speed, especially for the preparation of any free-hand patterns. It also has relatively high throughput and best-in-class accuracy with standard photoresists. It eliminates long turnaround time required for manufacturing and alignment of a mask. Additional advantage is the contact-free exposure and the possibility of a size reduction. Here, direct-write lithography is used for forming composite patterns for potential utility in biomedical implant devices and flexible electronics. The principle difference needs to be noted between the direct patterning techniques, when the material is directly deposited/removed or photo-modified, and the methods associated with direct-write lithography. The latter term ("direct-write lithography") is commonly reserved for maskless methods involving photoresists and is the technique used here. Both of them have substantial advantages and (potential) areas of use. One of the most attractive points of maskless direct-write lithography is its universality, which matches well with the universality of LBL assembly processes.

Single-walled carbon nanotube (SWNT) and gold nanoparticle LBL nanocomposites assembled with chitosan (CH) are made into prototypical patterns such as concentric helices and bus-line-and-stimulation pads (BLASP) used in flexible antennas and neuroprosthetic devices. Thus, using direct-write maskless lithography, a prototypical concentric spiral pattern from $(CH/SWNT)_{300}$ composite typically found, for instance, in RFID antennas is formed, as shown in FIGS. 17A and 17B. FIG. 17A is the as-fabricated pattern before etching, while FIG. 17B shows the patterned feature after oxygen plasma treatment. Similar patterns can also be used in negative refractive index optics.

Removal of the photoresists by etching does not disturb the pattern. The surface of the $(CH/SWNT)_n$ film (where n is the number of layers) is very uniform in macroscale, which is attributed to the nano- and microscopically homogeneous distribution of the SWNTs on the CH surface. In certain variations, the spatial resolution of this technique is established with the standard line grids to be at least 1 μm. Here, the width of the line is 1 μm, while the thickness of the composite films is about 520 nm. Gold nanoparticle films show particularly good accuracy and high resolution in direct-write patterning. The conductivity (resistivity) of the patterned composites is $6.45 \times 10^{-5}$ Ω·m and $3.80 \times 10^{-6}$ Ω·m at 20° C. for carbon nanotube and gold nanoparticle composites, respectively; in both cases it exceeds electrical parameters of similar composites and approaches the resistivity of graphite ($1.3 \times 10^{-5}$ Ω·m) indicating efficient charge transfer in the material and high interconnectivity of the nanotubes.

This value of resistivity of pristine non-doped $(CH/SWNT)_{300}$ films is more than two orders of magnitude lower than that of the polyaniline/SWNT composites with resistivity of $5 \times 10^{-3}$ Ω·m or all-nanotube LBL thin films with a resistivity of $1\times10^{-3}$ Ω·m. It is contemplated that charge transport in SWNT films can be further improved further by a variety of approaches including recently developed doping with via conjugation with π-bonds of aromatic polymers.

For more complex devices, this patterning method for nanocomposites with sequentially smaller features is tested. $(CH/SWNT)_{500}$ composite films are successfully patterned with orthogonal arrays of lines and bus-line-and-stimulation-pads (BLASP) patterns typical for implantable neurostimulation devices in FIGS. 18A-18B. In FIG. 18A, the widths of lines in the graded linear arrays are 100 µm, 90 µm, 80 µm, 70 µm, reduced in increments of 10 µm down to 10 µm, 9 µm, 8 µm, 7 µm, reduced in increments of 1 µm down to 1 µm. FIG. 18B is a detailed view of the circled portion of FIG. 18A. Microphotography in FIG. 18B shows that the smallest line width in the graded arrays and the smallest size of squares in the BLASP patterns obtained are 1 µm and 2.5 µm, respectively. Even smaller resolutions using these techniques are believed to be possible for these materials. There are no "meniscus corners" in the crossing parts; this fact indicates that the $(CH/SWNT)_n$ films exhibit excellent mechanical adhesion to the substrate. On the other hand, the round corners of the square contact pads in BLASP patterns indicate that a limit approached for the for direct-write patterning method. Although the BLASP pattern appears to be clearly defined, there are remnants of the SWNT composite in the etched areas. Thus, the etching step can be further optimized for $(CH/SWNT)_{500}$ films. To address its strong adhesion to the substrate, energetic and/or longer treatment with oxygen plasma can diminish adhesion and further improve resolution.

Patterns are also made for $(CH/Au\ NP)_n$ composite films, as shown in FIGS. 19A-19C. High quality patterns are made by direct-write lithography of the CH/Au NP composites. The surface of the $(CH/Au\ NP)_n$ film (where n is the number of layers) is highly reflective which is attributed to the homogeneously distributed Au NPs and high mobility of electrons. Indeed, the resistivity of the $(CH/Au\ NP)_{50}$ film is $3.80\times10^{-6}$ Ω·m at 20° C. This is more than one order of magnitude lower than resistivity obtained for SWNT films and two orders of magnitude higher than the resistivity of bulk gold, i.e., $2.05\times10^{-8}$ Ω·m. Resistivity of $(CH/Au\ NP)_{50}$ film composite is comparable to that of resistive alloys, such as nichrome, $1.10\times10^{-6}$ Ω·m. With respect to potential applications, such electrical properties combined with mechanical properties of composites and low temperature processing compatible with many plastics is exceptionally promising for flexible MEMS and actuators.

The smallest width of interconnecting lines for patterns on $(CH/Au\ NP)_n$ composites is again 1 µm and appears to be limited only by the resolution of the direct-write patterning instrument. The smallest 2.5 µm squares in the BLASP pattern have nearly ideal shape without any noticeable rounding or "meniscus corners." High-magnification optical micrographs do not show any remnants of the composite film on the glass substrate and therefore, indicative efficient and accurate etching process. Thus, such direct-write lithography processes can be used to form high-resolution, intricate and complex patterns in the inventive nanocomposite films, like those comprising gold nanoparticles.

In accordance with certain aspects of the present disclosure, creating flexible tissue-compliant implantable devices with at least two dimensions comparable to those of cells, namely thickness and width of the flexible strips, using LBL-made CNT nanocomposites is provided. Furthermore, new methods of implantation are also provided which enables insertion of the soft strips of nanocomposite into the brain tissue, which is a key challenge in this area. Two medical imaging techniques described in more detail below demonstrate that implantation results in electrodes positioned at the required depth so as to reach cortical areas of the rat brain. Finally, in vivo recording experiments are conducted to verify the functionality of the neural electrodes, which indicated successful registration of brain activity.

Various embodiments of the inventive technology can be further understood by the specific examples contained herein. Specific Examples are provided for illustrative purposes of how to make and use the compositions, devices, and methods according to the present teachings and, unless explicitly stated otherwise, are not intended to be a representation that given embodiments of this invention have, or have not, been made or tested.

Example 1

As noted above, previous comparative evaluation of IrOx and PEDOT with CNT composites concluded that CNT composite outperforms IrOx and PEDOT with respect to both electrical and mechanical properties upon cyclic excitation. Experiments are thus conducted to compare performance of certain variations of the inventive composite materials.

To provide a comparison between CNTs and Au NPs, the same technique of film preparation is used. The universality of the layer-by-layer (LBL) assembly offers this possibility. Compared to some other methods of thin film deposition, such as electrophoresis, chemical vapor, and solvent evaporation, LBL employs milder operating conditions, simpler instrumentations, and most importantly, provides a higher degree of structural control. It also permits the combination of organic and inorganic materials, which is important for biomedical applications. Last, but not least, LBL makes it possible to accurately control the thickness of the coatings by controlling the number of deposition cycles, n. This is particularly useful for the adequate comparison between Au NP and CNT film. LBL can be depicted as a versatile method to engineer multifunctional coatings down to the nanometer scale and to fine-tune the entire spectrum of materials properties: mechanical, electrical, optical, and biological to achieve the balanced combination specific for the particular application.

Therefore, LBL assembly is applied for the preparation of Au NP and SWNT composite thin films on electrodes. SWNT LBL films are assembled from SWNT aqueous dispersions stabilized by poly(styrene sulfonate) (PSS) using poly(vinyl alcohol) as a partner LBL polymer following the protocol described in Shim, Bong Sup, et al., "*Multiparameter Structural Optimization of Single-Walled Carbon Nanotube Composites: Toward Record Strength, Stiffness, and Toughness*," ACS Nano (2009), 3(7), pp. 1711-1722, and Shim, Bong Sup, et al., "*Integration of Conductivity, Transparency, and Mechanical Strength into Highly Homogeneous Layer-by-Layer Composites of Single-Walled Carbon Nanotubes for Optoelectronics*," Chemistry of Materials (2007), 19(23), pp. 5467-5474, both of which are hereby incorporated by reference in their entireties.

Au NP LBL films are made using concentrated citrate-stabilized NPs in water. In this variation, a standard polymer, poly(diallydimethylammonium chloride) (PDDA) is used as an LBL-partner. Polymers are selected that are electrochemically "silent" in the window of potential relevant for neural stimulation. Besides making it easier to understand the electrochemical performance of the coatings (as discussed below), having electrochemically inactive polymers as partners for NPs and CNTs helps avoid their redox decomposition, which is certainly undesirable.

High-purity single wall carbon nanotubes (P2-SWNTs) are used that are purchased from Carbon Solution, Inc. (Riverside, Calif.). Poly(vinyl alcohol) (PVA; MW 70 k), poly(sodium 4-styrene-sulfonate) (PSS; MW 100 k), and poly(diallyldimethylammonium chloride) (PDDA) are obtained from Sigma-Aldrich. All other chemicals are obtained from Sigma-Aldrich.

Synthesis of gold nanoparticles occurs via a standard citrate reduction method. Briefly, 90 mg of chloroauric acid ($HAuCl_4$) is dissolved in 500 mL of water. The solution is heated on a hot plate until boiling. Then 25 mL of 0.1% sodium citrate aqueous solution is added to the gold salt solution. The mixture is stirred and re-boiled on a hot plate. After 20 min, the solution becomes a red color, which indicates the formation of gold nanoparticles. The gold nanoparticles are concentrated 10 times (10×) by centrifuging at 9000 rpm for 50 minutes and removing 90% of the supernatant.

FIG. 10A shows a TEM image of as synthesized gold nanoparticles, while FIG. 10B shows an AFM image of dispersed carbon nanotubes. Transmission Electron Microscopy (TEM). TEM images are obtained using a JEOL 3010 TEM with acceleration voltage of 300 kV.

Layer-by-Layer assembly of Au NP Film and SWNT composite films is carried out on microscope glass slides cleaned in piranha solution overnight and then thoroughly rinsed with deionized water prior to the use. For LBL assembly, a glass slide is immersed in 0.1 wt. % solution of PDDA for 5 min, rinsed with DI water for 1 min, dried, and then immersed in concentrated Au NP solution for 10 min, rinsed for 1 min, and dried again. The procedure is then repeated with PDDA and Au NP solution.

SWNTs are first dispersed at 0.5 mg/mL in 2 mg/mL PSS (MW 100 k) solution by ultrasonication. The 0.1 wt. % PVA solution is prepared by dissolving correct amount of PVA in near boiling water. For each deposition cycle, the electrode is immersed in the PVA solution for 2 min, following by rinsing with deionized water and drying with an air jet. Then the electrode is immersed in SWNT solution for 5 min, following by rinsing with deionized water, and drying with an air jet.

FIGS. 11A-11B show high resolution SEM images of nanocomposite films comprising gold nanoparticles having a 300 nm scale and 500 nm scale respectively. For comparison, FIGS. 12A-12B likewise show high resolution SEM images of nanocomposite films comprising carbon nanotubes (with a 300 nm scale in FIG. 12A and a 500 nm scale in FIG. 12B).

From atomic force microscopy (AFM) images and ellipsometry data (FIGS. 1A-1D), Au NPs and CNT LBL films are successfully deposited in the sequential manner despite a complex film growth curve (FIG. 1D). FIG. 1A shows 15 bilayers of Au NP LBL film, while FIG. 1B shows 25 layers of CNT LBL film. FIG. 1C shows the first bilayer of Au NP formed by LBL. The Au NP LBL film displays a rough surface with close packed Au NPs. The surface morphology of the Au NP films can be described as globular, while the CNT films are fibrous with random orientation of the nanotubes within X-Y plane. Both nanoscale morphologies are important for increasing electrochemical surface area and improving the NPD performance. Scanning electron microscopy (SEM) images of Au NP and SWNT films also exhibit similar geometrical features (FIGS. 2A-2F).

Figures 2A, 2B, 2C, 2D, 2E, 2F:
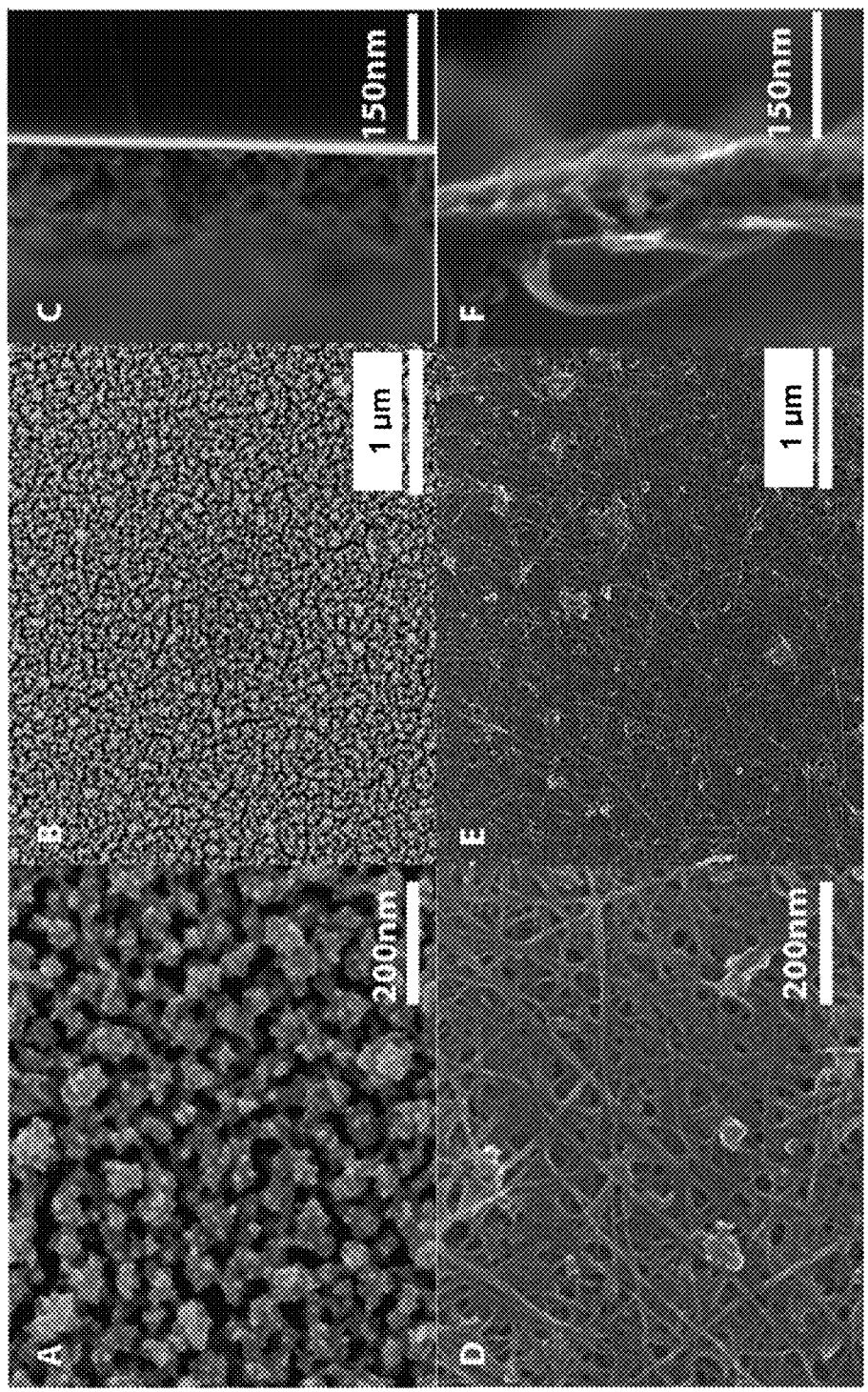

FIGS. 2A and 2B are SEM images of Au NP film according to certain aspects of the inventive technology at different magnification levels, while FIG. 2C is a cross-sectional image of Au NP film. Likewise, FIGS. 2D and 2E are SEM images of a CNT film at different magnification levels, while FIG. 2C is a cross-sectional image of CNT film. The SEM images are obtained using a FEI Nova Nanolab SEM at 10 kV accelerating voltage.

The total number of LBL deposition cycles is adjusted for both nanomaterials to obtain the same coating thickness. Cross-sectional SEM images for CNT and Au NP films (FIGS. 2C and 2F, respectively) obtained after 25 and 15 deposition cycles, respectively, show a thickness of approximately 100 nm±8 nm. The same images also indicate high content and interconnectivity of Au NP in the films.

Example 2

First, performance of the CNT coating is assessed. A wire electrode is fabricated and tested under the identical conditions to those in Shim, Bong Sup, et al., "*Multiparameter Structural Optimization of Single-Walled Carbon Nanotube Composites: Toward Record Strength, Stiffness, and Toughness*," ACS Nano (2009), 3(7), pp. 1711-1722, and Shim, Bong Sup, et al., "*Integration of Conductivity, Transparency, and Mechanical Strength into Highly Homogeneous Layer-by-Layer Composites of Single-Walled Carbon Nanotubes for Optoelectronics*," Chemistry of Materials (2007), 19(23), pp. 5467-5474, previously incorporated by reference above.

To further ensure accurate electrochemical measurements, a lithographic scheme to integrate LBL nanocomposite films into the microelectrode fabrication process according to certain variations of the present teachings is employed (as shown in FIG. 3A). The electrode design ensures that all films tested have the same surface area and their geometry is highly reproducible from batch to batch. The chosen microfabrication process (FIG. 3A) allows minimal exposure of the nanocomposite films to other process chemicals. EDAX spectroscopy indicates that the nanocomposite films are unaltered after the microfabrication process and that there are no residual chemicals on the surfaces of the films (See FIGS. 7A-7D).

More specifically, an LBL-Coated nanocomposite electrode is made that involves several standard microfabrication procedures. A substrate 110, such as a silicon dioxide glass slide is provided. Briefly, in step 2, a positive photoresist 112 (e.g., commercially available as SPR-220 3.0 from Rohm and Haas) is first deposited and then developed on the glass slide substrate 110. In embodiments where the gold nanoparticles are employed, metallic gold 114 can be deposited by e-beam or other conventional metallic deposition processes. For example, metallic gold 114 having a thickness of 500 nm is deposited by electron beam (Enerjet Evaporator, Denton) at a base pressure of $2 \times 10^{-6}$ Torr onto the photoresist-coated glass slide substrate 110. In alternative methods, carbon nanotube composites may instead be formed on the surface of the substrate 110 and over the photoresist 112 via techniques well known to those of skill in the art. Next, portions of the metal gold layer 114 are lifted-off in step 3. Thus, after evaporation, gold 114 is lifted off certain regions of the glass substrate 110 where the photoresist 112 is present by exposing the material to acetone to form the electrode layer.

Another deposition and development step 4 follows. Another positive photoresist 116, which may be the same as photoresist 112, is deposited over the available surfaces (over exposed gold layer 114 and exposed regions of substrate 110). The photoresist 116 is developed to form lift-off layer for the LBL film.

Next, in step 5, the nanocomposite LBL film 118 is deposited via an LBL assembly process applied over the metal layer 114 electrode. Once the LBL film 118 achieves a target thickness, the glass slide substrate 110 is transferred in acetone for LBL film lift-off in regions over the photoresist 116. Lastly, in step 6, a final layer of positive photoresist 120 is deposited and developed to form an insulating photoresist layer.

The impedance of the conventional CNT coating tested here is about 170Ω (compared to previously reported 277Ω) at the physically relevant frequency. In addition, the CSCs of the two coatings are also very similar, approximately 10 mC/cm².

Figures 7A, 7B, 7C, 7D:
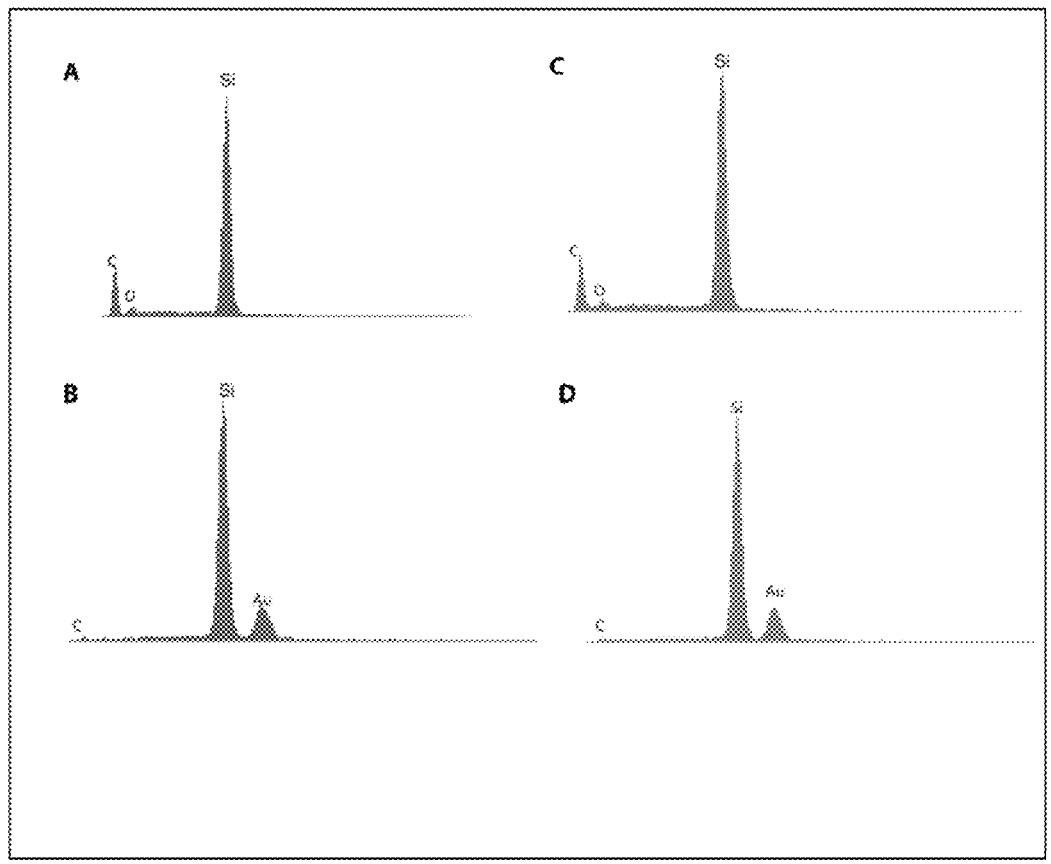

FIGS. 7A-7D show comparison between Au NP LBL composite films and CNT composite LBL films. FIGS. 7A and 7C show EDAX spectra of CNT films, while FIGS. 7B and 7D show Au NPs composite LBL films. FIGS. 7A and 7B are before microfabrication on a silicon substrate, while FIGS. 7C and 7D shows the surface after microfabrication on silicon substrates. Table 1 shows an AFM comparison of the Au NP and CNT LBL composite films.

TABLE 1

|  | Au NP film | CNT film |
|---|---|---|
| Mean Roughness | 7.386 nm | 10.376 nm |
| Surface Area | 9.474 μm² | 9.467 μm² |

Besides its convenience and accuracy, the design of these microelectrodes can be adapted to virtually any type of implants, including those with dimensions of less than or equal to about 10 μm.

Impedance (Z) and charge storage capacity (CSC) are investigated in a three-electrode electrochemical setup, which is most suitable for the measurement of these properties. Impedance is determined by electrochemical impedance spectroscopy (EIS). EIS is carried out on an Autolab PGSTAT 12; Frequency Response Analyzer software (EcoChemie, Utrecht, Netherlands) is used to record impedance spectra of the electrodes. A solution of 1 M phosphate buffered saline (PBS, pH=7) is used as an electrolyte in a three-electrode configuration. The working electrode is connected to the electrode site. The counter electrode is connected to a gold foil immersed in PBS, and an Ag/AgCl reference electrode is immersed in PBS. An AC sinusoidal signal of 25 mV in amplitude is used to record the impedance over a frequency range of 10-32,000 Hz. Impedance is measured by a frequency response analyzer from 10 Hz to 31 kHz. Au NP composite film has lower Z than SWNT composite film for the entire spectrum of frequencies relevant for NPDs.

Figures 4A, 4B:
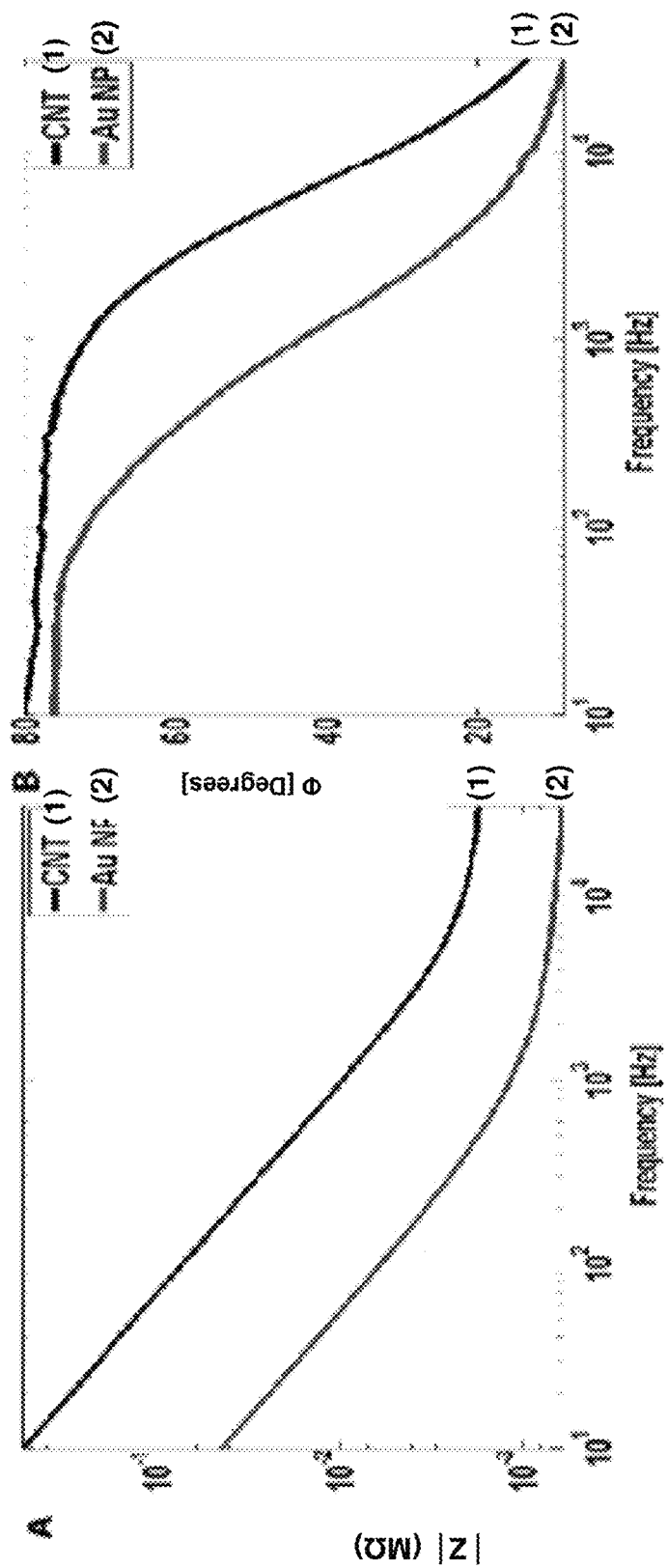

The characteristic impedance phase angles (Φ) for Au NP film across the entire frequency domain are smaller than SWNT film, which implies the higher conductivity of Au NP film (FIGS. 4A, 4B). This is further confirmed by the conductivity measurements in an ambient environment with a standard four-point probe. The conductivity of Au NP film is $8.6 \times 10^6$ S/m; this is more than a magnitude higher than conductivity of CNT film, namely $1.1 \times 10^5$ S/m. The area enclosed in the CV curve, S, of Au NP film is much larger than SWNT film for the same scan rate, v, indicating a substantially higher CSC.

Figures 4D, 4E:
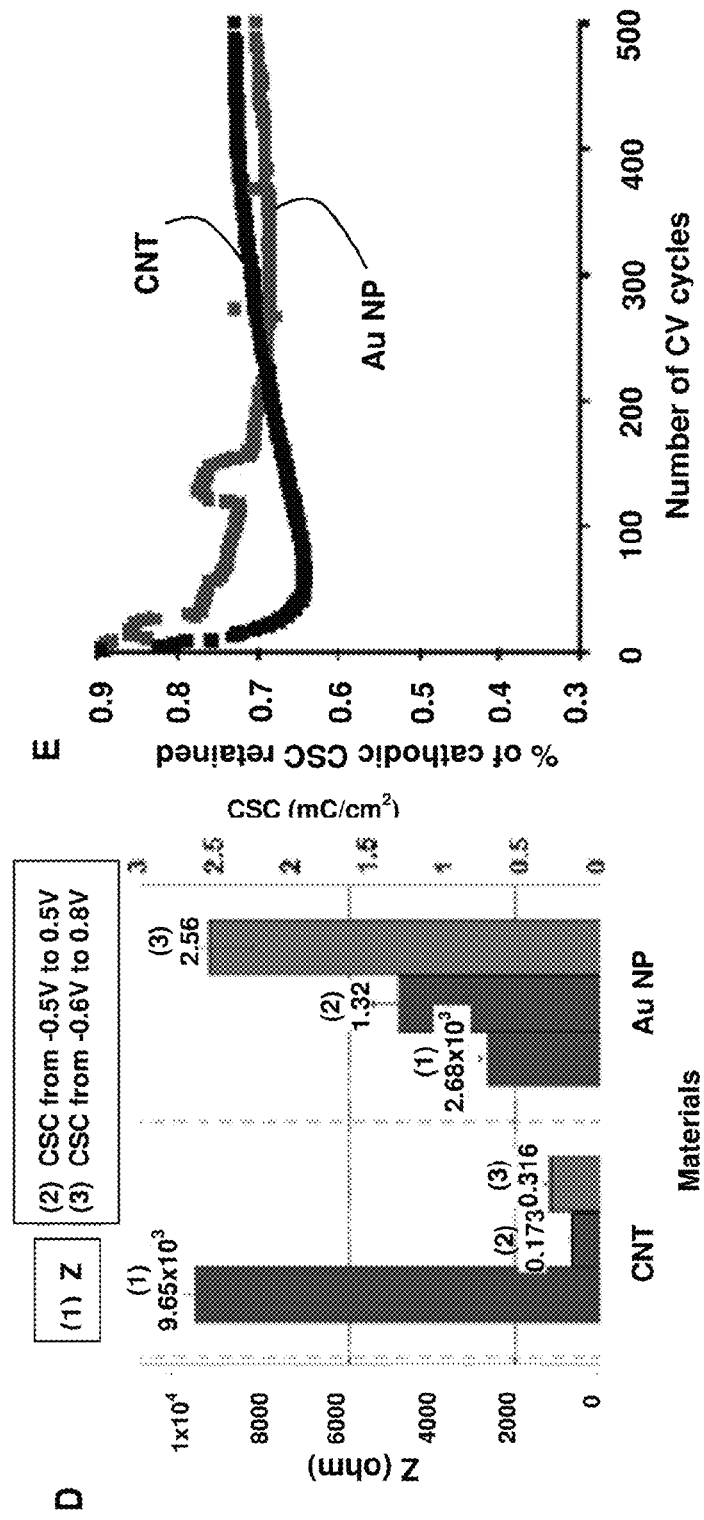
Figures 4C, 4F:
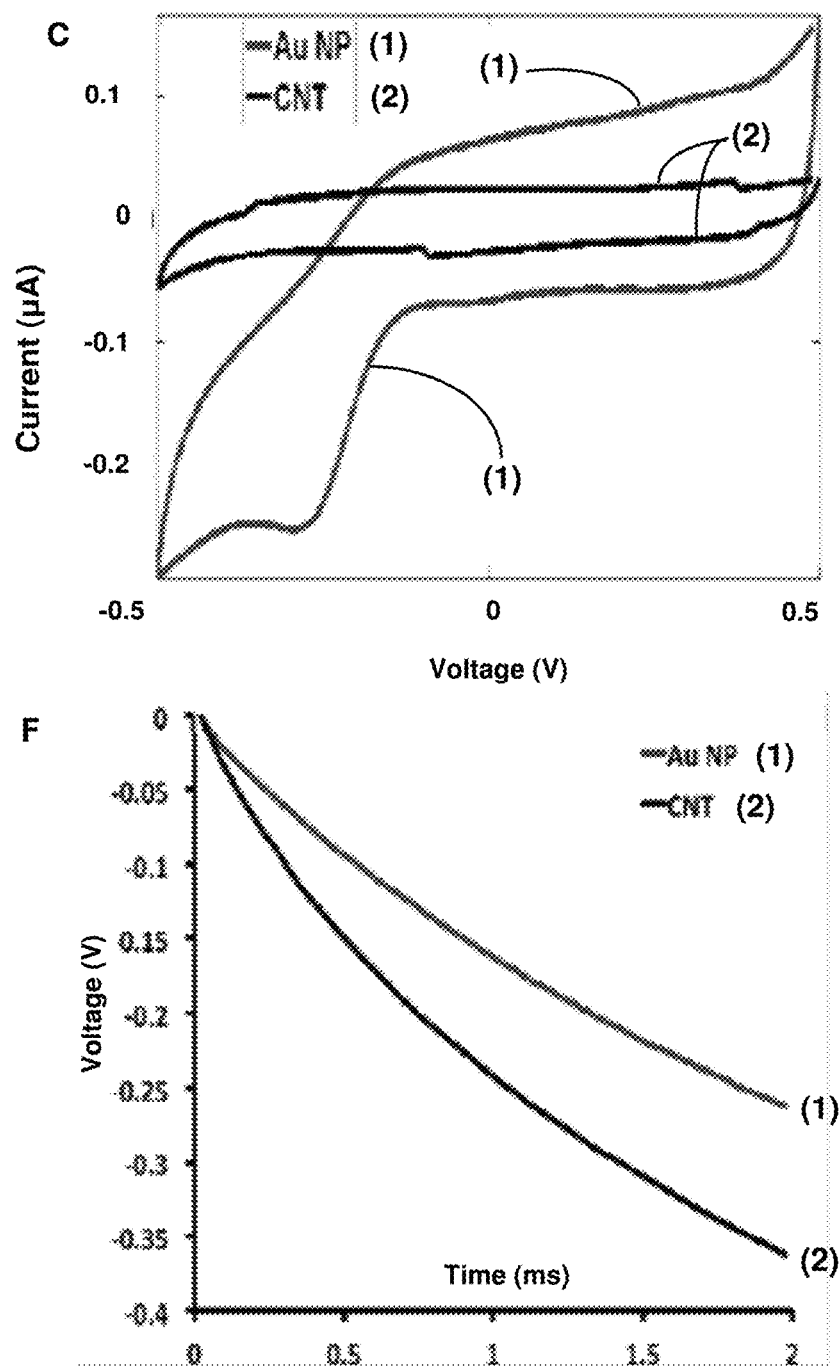

Detailed comparison of Au NP and CNT composite films are made by using impedance values measured for 1 kHz and cathodic CSC. In FIGS. 4D and 4F, the average measurements of 32 samples indicate that Au NP film outperforms SWNT film with respect to both Z and cathodic CSC. P-values for Z and CSC are less than 0.01 for a two-tail Student t-test, indicating that the differences between CNT and Au NP film are statically significant. The Z value of Au NP film is almost four times lower than SWNT film while the cathodic CSC of the Au NP film is close to one magnitude higher than SWNT film.

Total CSC is also quite informative although it is somewhat more difficult to compare. Previously, the total CSC of electrodes made from multiwalled carbon nanotubes, PEDOT, and IrOx have been reported. The total CSC of these materials for 100 nm thick coatings and a scan rate of 0.1 V/s from −0.9 to 0.5 V ranged from 6 to 9 mC/cm². Here, the total CSC of the 100 nm thick Au NP films at a scan rate of 1 V/s from −0.6 to 0.8 V is 2.56 mC/cm² (FIG. 4D). The actual voltage window is determined by the specific redox properties of the material and can be rarely matched exactly. The effect of the scan rate can be incorporated as a scaling factor because CSC is inversely proportional to the scan rate. Note that the width of the voltage window is, nevertheless, identical in each case and equal to 1.4 V. Recalculating the literature data to a 1 V/s scan rate scale shows that the total CSC for Au NP film is at least three times higher than analogous data in previous reports.

Example 3

Besides determining CSC, cyclic voltammetry (CV) experiments also offer additional information at the electrode/electrolyte interface. Cyclic voltammetry (CV) and voltage transients are performed using an Autolab PGSTAT 12 instrument and General Purpose Electrochemical System software (EcoChemie, Utrecht, Netherlands) in a three-electrode configuration as described above for EIS. For CV, a scan rate of 1 V/s is used and the potential on the working electrode is swept between −0.8 and 0.6 V. Three cycles are swept to ensure that the film has reached a stable state. For the voltage transient experiment, a cathodic current pulse (5 μA, 2 ms) is sourced and voltage changes are thus recorded during the experiment.

Thus, cyclic voltammetry of a nanocomposite comprising gold nanoparticles (Au NP) and PDDA with PBS solution and argon purges with PBS solution are conducted. A reduction peak in the CV curve of Au NP composite film is observed. In order to identify this reduction peak, a control CV experiment is conducted with argon gas purged PBS solution instead of regular PBS solution. The reduction peak disappeared after the argon purge of the PBS solution. This indicates that the peak is from the reduction of oxygen (see FIG. 8) observed on many metal electrodes, including gold electrodes.

Example 4

Furthermore, voltage transient experiments are conducted to evaluate the performance of Au NP composite film and CNT composite film. This technique is commonly used to determine the charge injection limit of an electrode for a given voltage limit. Cathodic current pulse (−5 μA, 2 ms) is applied to the electrodes while the voltage is recorded. For the same amount of charge, Au NP film has a lower voltage excursion compared to CNT film (FIG. 4F). This indicates that Au NP film has a high charge injection limit compared to CNT film for a given voltage limit. This result correlates well with the impedance data because lower impedance generally reduces over potential and lowers the voltage excursion.

Example 5

The circuit analogs of impedance data can be used to gain detailed insight about the materials properties and interfacial properties of an NPD. The circuit analog used here (shown in FIG. 5A) assumed the measured impedance is a product of electrical resistance of the film ($R_s$), charge transport losses at the film-electrolyte interface ($R_f$), and interfacial capacitance of the film ($C_d$). Walburg impedance (W) is previously included in many analog circuits as well. However, W is only relevant for systems with strong mass transport limitations. For the operating environment of NPDs, one can consider that the transport limitations to be minimal due to the large amount of ions present and the small amount of charge transferred. By fitting the impedance data using this circuit analog (FIG. 5A), the experimental impedance Z is lower for the Au NP composite film (FIGS. 4A, 4D) due to the lower $R_s$ and $R_f$. The high CSC values for Au NP composite films can be correlated with high value of $C_d$. This indicates that the high surface area created by NPs and the high interconnectivity among NPs in the composite materials play important roles in determining the macroscale electrochemical functionalities. It can also be important to note that CSC of solid noble films is typically low. Platinum/iridium alloy, which is the best choice for metallic neural electrode, only has a theoretical maximum CSC of 0.3 mC/cm$^2$, and the CSC of pure metallic Au is even lower. Notably, the marginal CSC of noble metals prevents the possibility of fabricating high-performance stimulating microelectrodes from the classical evaporation plus microfabrication techniques.

Example 6

To further evaluate the feasibility of LBL composite films in neural interface applications, electrochemical stability tests are conducted for both Au NP and SWNT LBL films. As noted above, SWNT films have remarkable environmental resilience and thus are selected for illustrative purposes. Therefore, both films are subjected to a 500 CV scanning cycle at a fast scan rate of 1 V/s. As illustrated in FIG. 4E, the CSC of both films decreases initially, then stabilizes around 400 cycles. This demonstrates that Au LBL films offer similar stability compared to SWNT films, which is quite remarkable considering the exceptional mechanical properties of individual CNTs and the fact that they have virtually perfect planar orientation in LBL films (FIG. 1D), which provides the best translation of their mechanical properties to the composites.

Example 7

Besides excellent electrochemical properties, neuron adhesion/surface biocompatibility is also important for high quality in vivo recording. A close interface between electrode/neuron improves the quality of the recording. In this example, the biocompatibility of the Au NP/PDDA coating is tested with in vitro culture of NG108-15 cells, a type of mouse neuroblastoma/glioma hybrid cells, which are typically used in many biocompatibility/toxicity protocols. Cells are seeded and cultured on glass slides coated with Au NP/PDDA film.

The NG108-15 cell line is obtained from American Type Culture Collection (ATCC, HB 12317). The cells are cultured with Dulbecco's Modified Eagle Medium (DMEM) high glucose media (commercially available from Gibco as product 11965-092) and hypoxanthine-aminopterin-thymidine supplement (ATCC, 69-X)+10% fetal bovine serum at 37° C. with 5% $CO_2$. Once the cells reach 90% confluence, they are detached from the culture flask and 1×10$^6$ cells are seeded onto a 1 cm×1 cm glass slide coated with Au NP/PDDA film. The cells are cultured in the same conditions for three days on the glass slide before the biocompatibility test.

The biocompatibility of the Au NP/PDDA films is tested by a Live/Dead Biohazard Cell Viability Kit (Invitrogen, L-7013) according to the exact protocol provided the vendor. Then, the live and dead cells are counted and cell viability is calculated by dividing the number of live cells by the total number of the cell on the substrate.

Figures 5A, 5B, 5C, 5D:
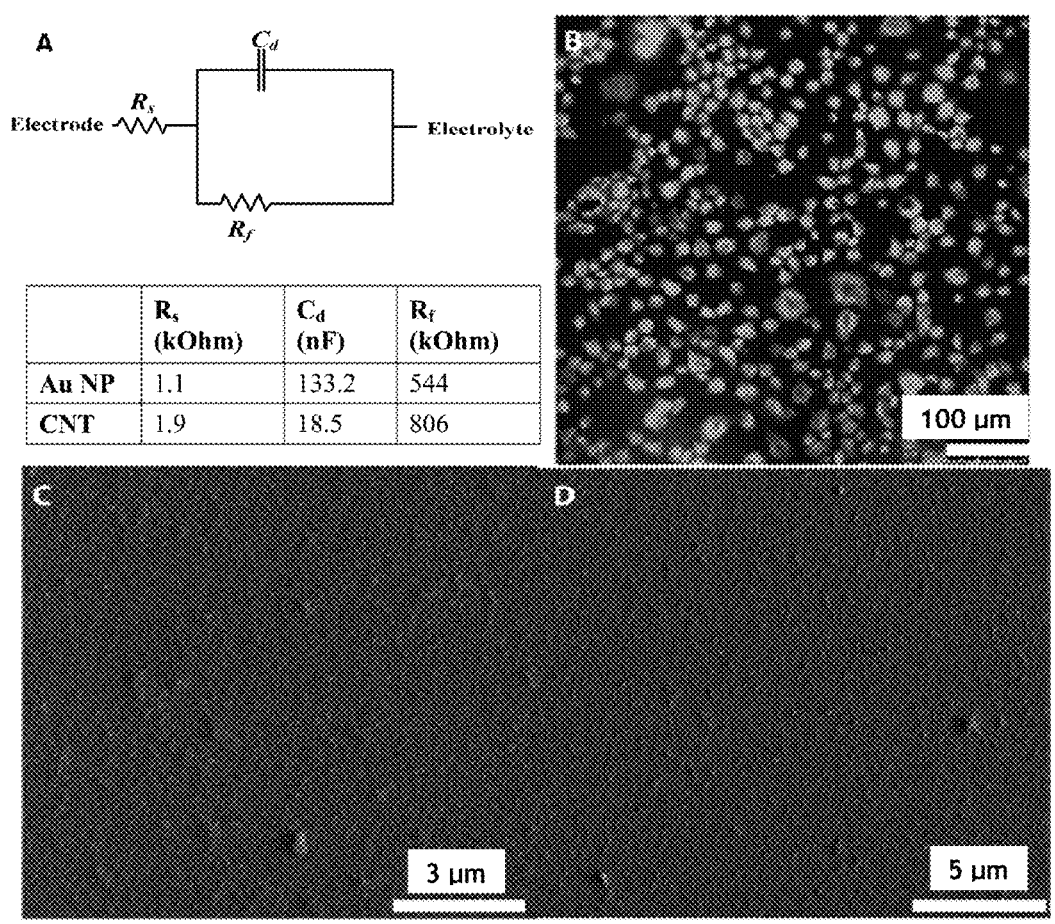

Optical images showed NG108 cells could adhere well on the coating and differentiate into neuron-like morphology (see FIGS. 9A-9B). FIG. 9A shows an optical image of pre-differentiated NG-108 cells, while FIG. 9B shows differentiated NG-108 cells on Au NP/PDDA film. A Live/Dead assay is also performed and indicated that 99.9% of cells are live on the surface of the Au NP/PDDA coating (FIG. 5B).

Additionally, the mechanical integrity of Au NP film is also examined by an ex vivo insertion test. The electrodes coated with Au NP/PDDA are inserted into a fresh harvested rat brain and kept at 4° C. for 3 days. Then the electrodes are removed from the brain, rinsed with PBS, and imaged with SEM. The Au NP/PDDA coating surface retains the same nanoscale roughness as observed before the insertion (FIGS. 5C-5D).

Example 8

In this example, tissue-integrated devices comprising a CNT nanocomposite according to certain aspects of the present disclosure are demonstrated. More specifically, flexible neural electrodes are microfabricated using microelectromechanical systems (MEMS) technology and implanted into rat motor cortex. Further, tissue localization has been successfully visualized with MRI and photoacoustic imaging. In vivo evaluation demonstrated the functionality of such neural electrodes by successful registration of brain activity.

During the implantation procedure, the neural electrode needs to be delivered to the specific region of interest, while also avoiding blood vessels to minimize bleeding. This requires close assessment of the insertion site and the spatial arrangement of the electrode within the brain tissue. The state of the electrodes after implantation is then examined by two imaging modalities: photoacoustic microscopy (PAM) and magnetic resonance imaging (MRI). PAM combines optical and acoustic imaging techniques to produce images with excellent optical contrast and great imaging depth. It would be an excellent tool for monitoring vasculature. On the other hand, MRI is a well-established technique that can provide a non-invasive and high depth 3D image of the nanocomposite electrodes inside the brain.

Figure 13A:
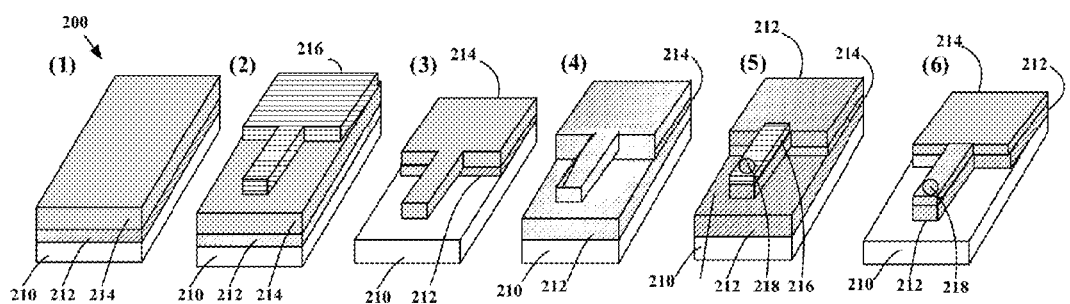

A first challenge to small tissue-compliant nanocomposite electrodes is developing microfabrication techniques adequate for both the starting material and the final implantable device. In other words, it is a goal to integrate layered CNT nanocomposites with established microfabrication and MEMS technologies to produce functional electrodes without use of silicon. The flexible nanocomposite neural electrodes according to certain aspects of the present disclosure can be fabricated using a two-mask process 200 with optical photolithography technique, as illustrated in FIG. 13A.

In step 1, a substrate 210 is coated with parylene-C 212, followed by deposition via layer-by-layer to form a nanocomposite layer 214 comprising conductive nanoparticles and a matrix material. For example, 800 nm of parylene-C thin film 212 is first deposited by chemical vapor deposition method (PDS 20350, SCS Equipment) on a clean glass slide substrate 210. The first layer of parylene-C 212 serves as the bottom insulation layer for the electrode device. For example, the nanoparticles may be carbon nanotubes and the matrix may comprise poly(sodium 4-styrene-sulfonate) (PSS) and poly (vinyl alcohol) (PVA). High purity single wall carbon nanotubes (P2-SWNTs, >90% purity) are obtained from Carbon Solution, Inc. (Riverside, Calif.). Poly(vinyl alcohol) (PVA; MW 70 k Fully hydrolyzed) and poly(sodium 4-styrene-sulfonate) (PSS; MW 100 k) are obtained from Sigma-Aldrich. All other chemicals are obtained from Sigma-Aldrich.

Layer-by-Layer Assembly of SWNT nanocomposite layer 214 is initially carried out on microscope glass slide substrates 210 cleaned in piranha solution (mixture of sulfuric acid and hydrogen peroxide) overnight and then thoroughly rinsed with deionized water prior to the use. SWNTs are first dispersed at 0.5 mg/mL in 2 mg/mL PSS (MW 100 k) solution by ultrasonication. A 0.1 wt. % PVA solution is prepared by dissolving the correct amount of PVA in near boiling water. For each deposition cycle, the electrode is immersed in the PVA solution for 2 min, following by rinsing with deionized water and drying with an air steam. Then, the electrode is immersed in SWNT solution for 5 min, following by rinsing with deionized water and drying with an air jet. The cycle is repeated for 300 times by Nanostrata (nanoStrata Inc., Tallahassee, Fla.). The CNT:PSS/PVA nanocomposite layer 214 is deposited over the parylene-C film 212 using the layer-by-layer (LBL) assembly method until it has a thickness of 1 μm.

In step 2, after the parylene-C layer 212 and CNT nanocomposite 214 deposition, a positive photoresist 216 (SPR220-3.0, Rohm Haas) is spin coated and exposed by the first mask on the CNT composite layer 214. After developing the photoresist 216, the CNT composite 214 and the bottom layer of parylene C 214 are etched by oxygen plasma (790 RIE, Plasma Therm) in step 3. This step patterns the base layers of the neural electrode. After the oxygen plasma etching in step 3, a second layer of parylene-C 214 is deposited onto the base layer 214. This serves as the top insulation layer for the neural probe. Then, in step 5, positive photoresist 216 is spin coated again and exposed by the second mask on top of the second layer of parylene-C 214. The entire substrate is etched slowly by oxygen plasma to avoid over-etch of the CNT composite 214. The second mask creates the outline for the final electrode shape and opens the functional CNT composite site 218 at the tip of the electrode.

Figure 13B:
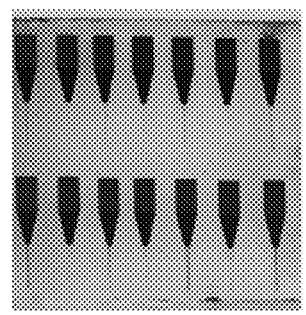

Compared to the processes of the previous approaches used for fabricating metal/polymer flexible electrodes, this method eliminates the additional steps of lift-off and wet etch of metal. A second layer of parylene-C 214 is deposited after the plasma etching to serve as the top insulation layer for the neural probe. The entire substrate is etched slowly by oxygen plasma to avoid over-etching into the CNT composite layer 214. The electrodes are thus fabricated on glass substrates 210 and are lifted-off from the substrate 210 with hydrofluoric acid (HF) to produce free-standing devices after wire bonding to the circuit lead (not shown). The implantable region of the nanocomposite electrode had a thickness of 3 μm, which is much smaller than typical cell dimensions and provided the electrodes with required flexibility (FIG. 13B).

The width of the electrode—the second dimension that is desirably comparable to or smaller than the size of neuron—is varied in this study between 10 μm and 50 μm. Each different size of electrode also had a different size of functional recording site, which varied from 100 μm$^2$ to 2500 μm$^2$. Their length is 5 mm, which is sufficient to reach deeper structures within the rat brain.

Figure 13C:
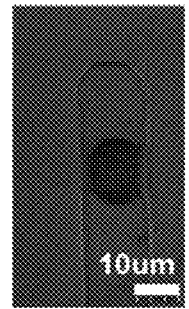
Figure 13D:
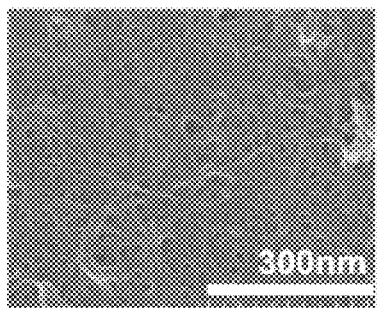

The final electrodes formed by the methods described above are examined by scanning electron microscopy (SEM) (FIG. 13C). (SEM) images are obtained using a FEI Nova Nanolab SEM at 10 kV accelerating voltage. The recording site at the tip of the electrode is 10 μm×10 μm in size, while the rest of the composite electrode is well insulated by parylene-C. A zoomed-in image of the functional site shows that the integrity of the CNT composite is preserved through the fabrication process (FIG. 13D).

After successful fabrication of the electrodes, electrochemical tests are carried out to characterize the functionality of the neural electrode. The electrochemical performance in terms of impedance (Z) and charge storage capacity (CSC) is measured in a three-electrode electrochemical set-up and calculated with a custom MATLAB (Mathworks Inc., MA) script. The exact Z and CSC needed for NPDs depend on neural tissues and the type of the projected treatment/interface. Nevertheless, the minimization of Z and maximization of CSC are the typical requirements for implantable electrodes as they reflect the key electrochemical parameters for their reduction of noise in NPDs, reduction of electrical damage to the tissue, and improving their long-term performance. As discussed above, meeting these parameters for electrodes of small dimensions represents the key challenge for traditional NPD materials and could be used as the quality control test.

Impedance is measured by a frequency response analyzer from 10 Hz to 31 kHz for three different sizes of electrodes (FIG. 14A). As expected, a negative correlation between electrode size and impedance is observed because larger electrodes have higher electrical conductance and larger surface area for the functional site. The impedance decreases as the voltage frequency increases, which is also expected from the resistor/capacitor model for impedance because impedance is inversely related to frequency. Capacitive response dominates the impedance values at high frequencies.

Cyclic voltammetry (CV) curves obtained at a scan rate of 1 V/s from −0.6 V to 0.8 (FIG. 14B) are used to calculate CSC. For numerical comparison among electrodes of different sizes, the impedance magnitude of the electrodes at 1 kHz is plotted, which is the physiological relevant neural spiking frequency and the total amount of charge injected by integrating the area enclosed in the CV curve, which is a key parameter for neural stimulation (FIG. 14C). The correlation between electrode size and electrochemical properties indicates the precision over the control of the electrode's functional site.

The softness and flexibility of the implantable nanocomposite electrode devices became a major challenge during the electrode insertion into the brain. Thus, the present disclosure contemplates several methods that overcome this challenge, such as using an additional water-soluble layer polymer/protein to temporarily stiffen the probes and chemically modify probe-releasing shuttles. To avoid extensive chemical modification and enable the in-vivo experiment, electrode-releasing shuttles based on simple capillary interactions between the nanocomposite strip and a microscale stainless steel needle (shuttle) are applied for electrode insertion.

In certain variations, methods of preparing a neural prosthetic device for implantation into a brain of an animal are contemplated. The method optionally comprises cooling a shuttle and an implantable electrically conductive device that comprises a flexible, electrically conductive, implantable region that comprises a nanocomposite material, as in any of the embodiments described in the present disclosure. Any shuttle known in the neural implantation arts is contemplated, such as a stainless steel needle, for example. The shuttle and implantable electrically conductive device may be cooled within a cold environment, for example, having a temperature of less than or equal to about 0° C. In certain variations, the shuttle and implantable electrically conductive device may be freeze dried, e.g., exposed to an environment having a temperature of less than or equal to about −10° C. to about −100° C. at atmospheric pressure conditions. Next, the shuttle and the implantable electrically conductive device are heated to a temperature that facilitates condensation of water from the surrounding environment onto a surface of the flexible, electrically conductive, implantable region and on a surface of the shuttle. In certain variations, the shuttle and implantable electrically conductive device are heated to greater than or equal to about 20° C. at atmospheric pressure. Next, the surface of the shuttle having the condensation formed thereon is brought into contact with the surface of the implantable electrically conductive device having condensation thereon. Thus, when the shuttle and implantable electrically conductive device are contacted with one another, condensed water is disposed there between. Next, the shuttle and the implantable electrically conductive device are cooled to a temperature of less than or equal to about 0° C., so that the water freezes the shuttle to the implantable electrically conductive device, thus forming a neural prosthetic device assembly capable of implantation into the brain of the animal. In certain variations, the shuttle and implantable electrically conductive device may be freeze dried, e.g., exposed to an environment having a temperature of less than or equal to about 0° C. or optionally less than or equal to about −10° C. After the chilled neural prosthetic assembly is implanted into the animal, the frozen water will melt and the shuttle can be separated from the implantable electrically conductive device and removed, while the implantable electrically conductive device remains within the animal's brain.

Figure 16A:
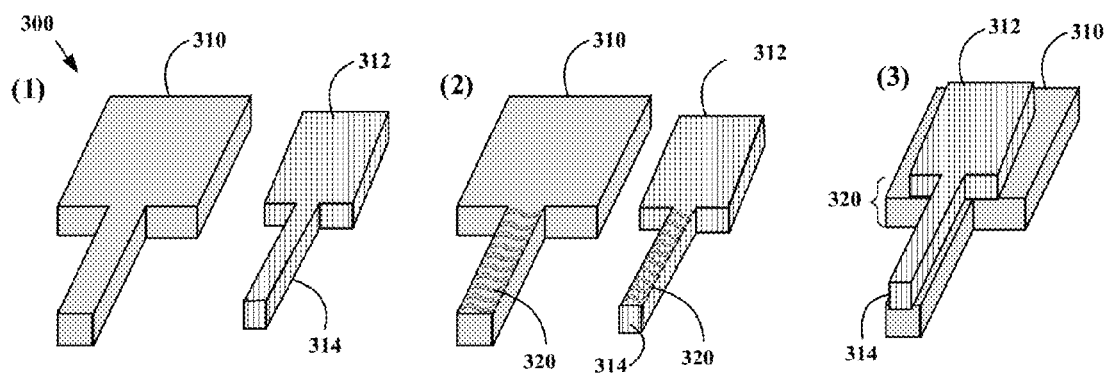
Figure 16B:
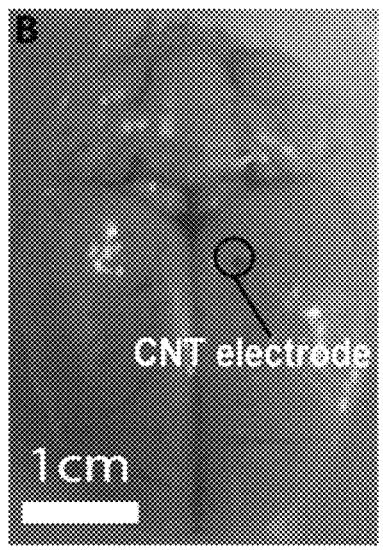

The exemplary procedure 300 is illustrated in FIG. 16A. In step 1, a shuttle 310 (a thin metal needle, which may be formed of stainless steel) and an implantable flexible electrode device 312 having an implantable region 314 (formed of a nanocomposite strip prepared in accordance with certain aspects of the present disclosure) are freeze dried. The flexible electrode device 312 and the shuttle 310 can be stored in dry ice for at least an hour. Then, in step 2, a water condensation step occurs, where the flexible electrode device 312 and shuttle 310 are removed from the dry ice and kept at room temperature until water 320 condenses on both the flexible electrode device 312 and shuttle 310. In step 3, the flexible electrode device 312 having the implantable region 314 (e.g., composite strip is placed on top of the shuttle 310 so that the flexible electrode device 312 and shuttle 310 adhere to one another via condensed water to form an assembly 320. After step 3, the entire assembly 320 is stored in dry ice again, ready for the implantation procedure. While not shown in FIG. 16A, after the craniotomy on an animal is performed, the electrode/shuttle assembly 320 is removed from the dry ice and quickly inserted into the brain tissue. When the interfacial ice layer between the shuttle 310 and flexible electrode device 312 melts, the shuttle 310 is then removed while the flexible electrode device 312 remains inside the brain.

Example 9

After verifying the electrochemical performance of the as-fabricated neural electrodes and carefully assessing the state of the neural electrodes, in vivo physiological recording experiments with rats are conducted. The typical procedure of the animal preparation and neural recording is as follows. Adult male Sprague-Dawley rats (Charles River Laboratories) 550-600 g are anesthetized with 2% isoflurane. The depth of anesthesia is observed by monitoring heart rate and blood oxygen saturation. The animal is placed into a stereotaxic frame and a 2 mm by 2 mm craniotomy is made over the motor cortex. Once the dura is incised and resected, the animal brain is ready for implantation. The implantable neural probe is inserted into the brain tissue as described above.

In-vivo electrophysiological data are recorded using a TDT RX5 Pentusa Recording System (Tucker-Davis Technologies, Alachua, Fla.). These neuronal signals are acquired through a head-stage buffer amplifier to avoid signal loss in data transmission. Signals are sequentially filtered by an anti-aliasing filter in the preamplifier, digitized at a ~25-kHz sampling rate, and digitally band-pass filtered from 2 to 5000 Hz. Wideband signals are acquired to capture both spiking and LFP activity. Signals are continuously recorded in 10 minute intervals. Neural recording segments are analyzed offline using custom automated MATLAB (Mathworks Inc., MA) script. The local field potential (LFP) power spectral density plots are created using a Hamming window for smoothing with a 32768-point fast Fourier transform (FFT).

Figures 15A, 15B, 15C, 15D, 15E:
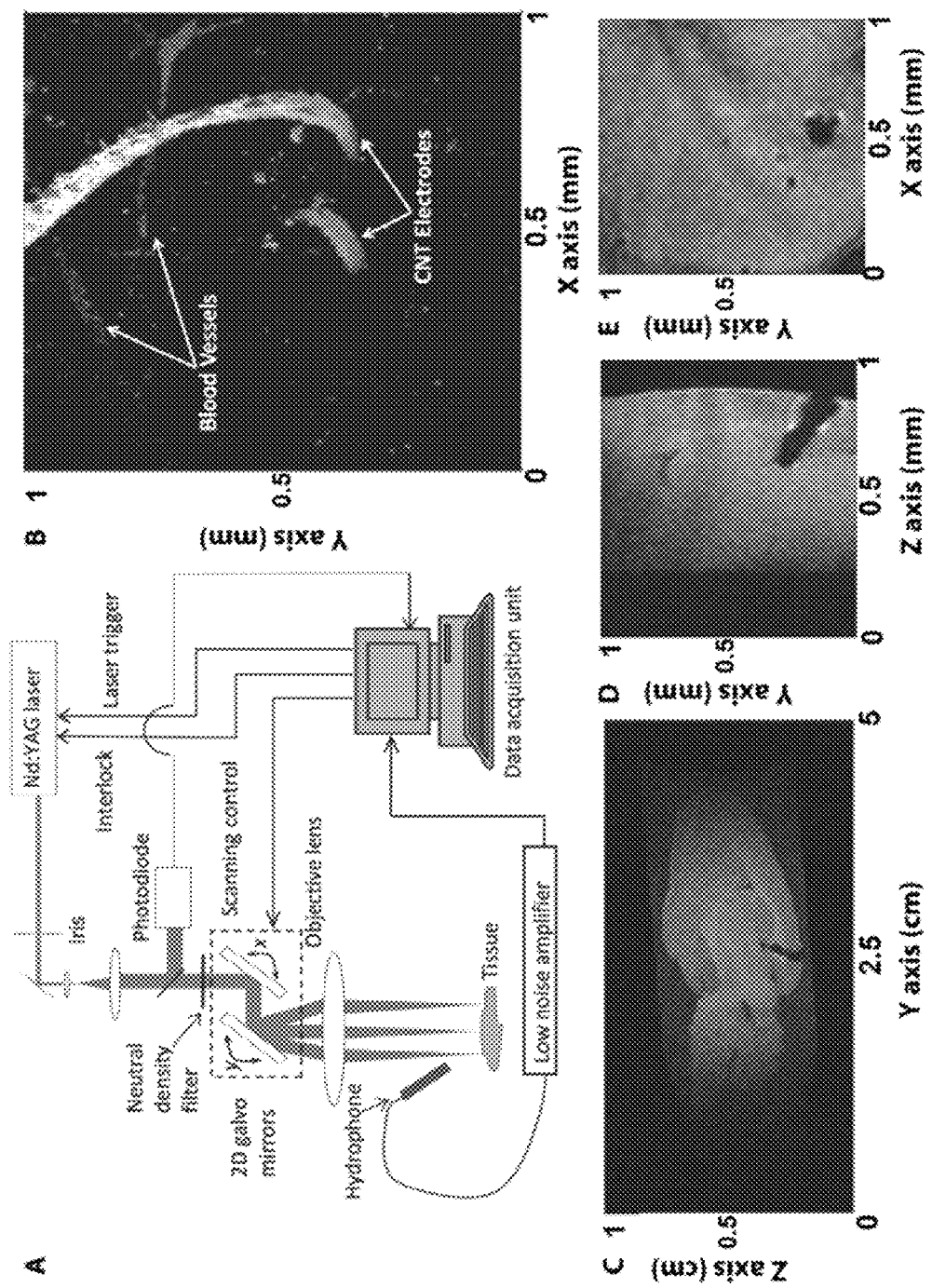

Photoacoustic Microscopy are carried out through a Nd:YAG laser (Spot-10-200-532, Elforlight Ltd, UK) working at 532 nm with a pulse duration of 2 ns and a repetition rate (PRR) of 0-50 KHz, as shown in FIG. 15A. The laser light is spatially filtered by an iris and then expanded to a parallel beam, which is rastered over the tissue object by 2D Galvanometers. The intensity and the stability of the laser beam is monitored and calibrated by a photodiode (DET10A, Thorlabs, NJ). An achromatic lens with a focal length of 50 mm is used as the objective lens. Photoacoustic signals are detected by a calibrated needle hydrophone (HNC-1500, Onda, CA) with −10 dB bandwidth of 300 kHz-20 MHz. The distance between the hydrophone and the tissue is 5 mm, and the ultrasound coupling is through water. The detected photoacoustic signals, after a low noise amplifier (AH 2010, Onda, CA), is digitized by an A/D card (Razor CS14X2, GaGe, IL). The spatial resolution of this system is measured by imaging an USAF resolution template (T-20-P-TM, Applied Image Inc, NY). The lateral resolution is 5 µm, determined by the optical focusing. The axial resolution of this system is 105 µm, which is limited by the central frequency and bandwidth of the hydrophone.

Magnetic Resonance Imaging (MRI) is performed with a 3D gradient echo pulse sequence at 2.0 T (Varian Inc., Palo Alto, Calif.) using a home built RF coil. Data are obtained with TR=100 ms and TE=10 ms, and with 100 microliter isotropic voxels. Following acquisition, the data are processed by scripts written in Matlab (The Mathworks, Natick, Mass.).

For chronic neural implants, the state of the implanted neural electrode needs to be frequently evaluated both during and after implantation. It can also be important to verify that the insertion of the flexible electrode occurred without wrinkling or tears. The PAM technique is based on the difference of optical absorption in tissues and is realized by rastering laser beam over the brain tissue (the PAM apparatus setup is shown in FIG. 15A). Photoacoustic signals are detected by a calibrated needle hydrophone and the ultrasound coupling is through water. With this imaging system, lateral resolution of 5 µm and axial resolution of 105 µm is achieved.

FIG. 15A represents a typical PAM image of the implantable nanocomposite electrode device according to certain aspects of the present disclosure inserted into the brain tissue. Due to its strong optical absorption, the nanocomposite electrode devices display high contrast in the image. The insertion site of the electrodes is easily identified. Moreover, the vasculature in the brain tissue can be visualized due to strong absorption of hemoglobin, which is very important for electrode insertion. PAM makes possible high resolution mapping of blood vessels in the brain tissue, which can be utilized to minimize their rupture during the insertion procedure, thus reducing insertion damage and preserving neurons. Combining electrodes with high PAM contrast image of blood vessels is a valuable tool for clinical neural surgery.

Assessing implanted flexing neural electrodes inside of the brain during and after the surgery is also important. MRI images after implanting the compliant implantable electrode device formed of a nanocomposite comprising nanotubes according to certain variations of the present disclosure are shown in FIGS. 15C-15E. The high contrast of the flexible implantable nanocomposite electrode is attributed to both the loss of water proton and disturbance of the magnetic field created by the nanocomposite electrodes. FIG. 15C is the cross-sectional view of the electrodes implanted in the brain. The implantation procedure discussed above successfully delivers the implantable electrode device into the brain without any kinks or curvature. FIGS. 15C-15D. FIG. 15E is the zoomed out image of the cross-sectional view. The position of the electrode and the depth of the electrode in the brain are thus identified.

Figures 16C, 16D:
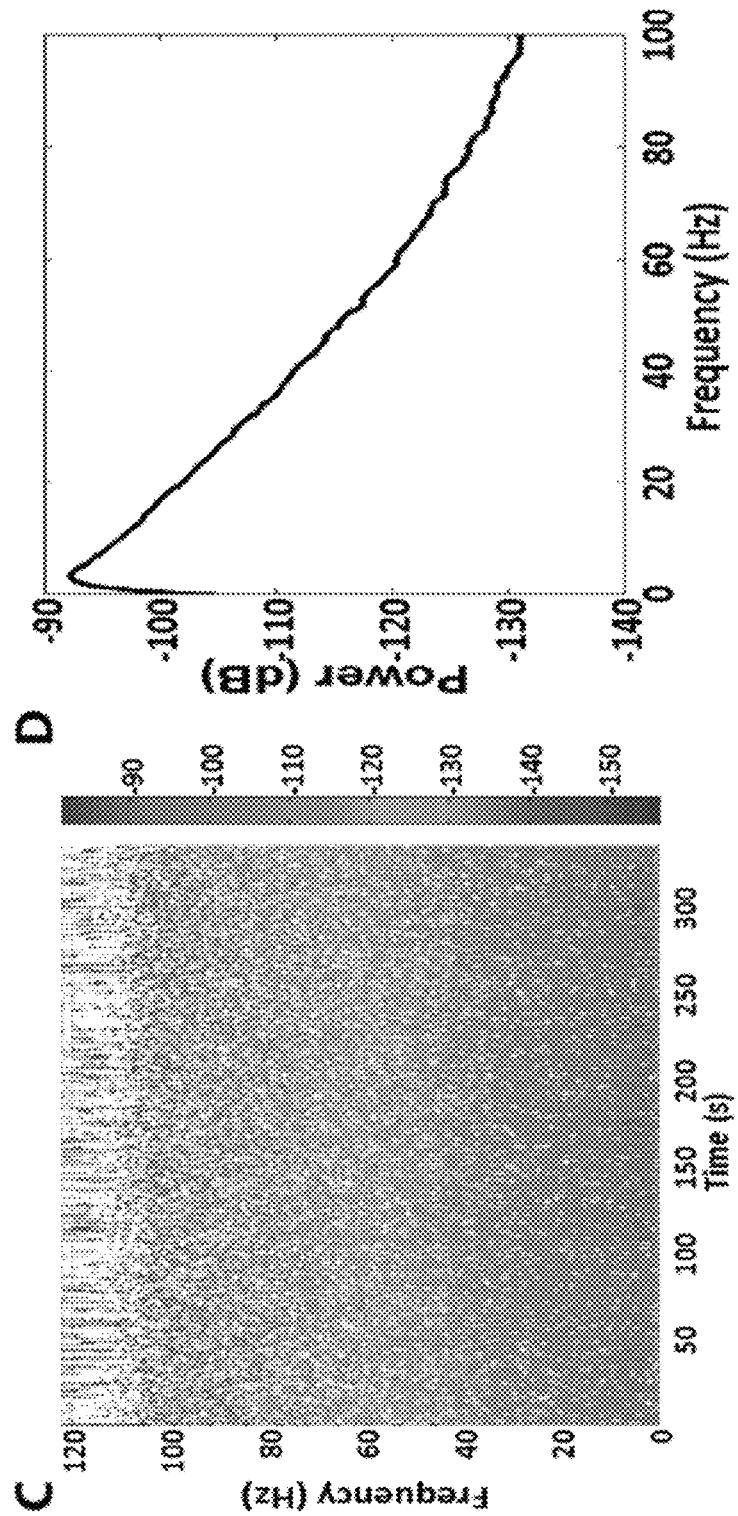

FIG. 16C is the typical local field potential recorded over time for the implanted neural probes. The spectrum of the plot represents the intensity of the local field potential. The electrode records low frequency signals between 0 to 20 Hz consistently over time. To further identify the frequency of the local field potential, the intensity data over time is accumulated to generate a power spectrum. The power spectrum shows a peak around 5 Hz. No intensity peak at 60 Hz is observed, which is common for instrumental background noise. The power spectrum clearly demonstrates that the neural electrode could specifically identify the low frequency neural signal from instrumental noise.

This example demonstrates that LBL assembly is capable of producing tissue-compliant nanocomposite implantable devices with exceptional electrochemical performance particularly suitable for neuroprosthetic devices. In this variation, the nanocomposites comprise nanotubes and structurally form the implantable region of the implantable device. These nanocomposites can be microfabricated with required precision using standard photolithography technology into flexible implantable neural electrode devices. The footprint of the electrodes can be miniaturized to 10 µm in width with thicknesses as small as 3 µm, which is smaller than any known conventional stiff or flexible functional NPDs. The low frequency neural signal is recorded in the animal model to demonstrate the functionality of the neural electrodes. Emerging and well established imaging modalities examine these flexible neural electrodes in the brain. These results advance nanocomposite-based flexible neural prosthetics in a clinical setting. Given the flexibility of neural electrode devices comprising nanocomposites, the implantation procedure and methodology requires specialization for routine usage.

Quite unexpectedly, the inventive nanocomposite films prepared in accordance with certain aspects of the present teachings have remarkable charge transfer capacity, substantially lower impedance and comparable electrochemical stability under fast voltage scans. In particular, Au NP-based and CNT-based nanocomposites are provided that have desired characteristics for the next generation of implantable neuroprosthetic devices (NPDs). Besides the superior electrochemical performance, additional advantages of variations of nanocomposites comprising Au NP prepared in accordance with certain aspects of the present teachings, as compared to other (nano)materials, include without limitation: (1) the long-standing clinical record of gold in both nano- and macroscale forms facilitates their acceptance for use in medical uses; and (2) LBL assembly is a flexible process that offers tremendous possibilities for further optimization and adaptation to additional NPD functions, which for instance can include in situ gene delivery. The present disclosure further contemplates using LBL films with novel Au NPs materials, such as nanoshells and nanostars.

Thus, in various aspects, the present disclosure provides a general microfabrication process for Au NP or CNT LBL composite films or implantable structures suitable for preparation of ultra-small implantable electrodes that can be virtually "invisible" to the immune system. Integration of LBL film deposition technology and traditional lithography provides many possibilities for utilization of nanostructured LBL composites from NPs and their unique properties in many applications. Thus, the present teachings contemplate fabrication of microelectrodes, which are mechanically compliant with the soft neural tissues. A flexible and high-performance electrode comprising Au NP or CNT materials provides the ability to minimize tissue stress and provide long-term stability for future implantable neural prosthetic devices.

The foregoing description of the embodiments has been provided for purposes of illustration and description. It is not intended to be exhaustive or to limit the disclosure. Individual elements or features of a particular embodiment are generally not limited to that particular embodiment, but, where applicable, are interchangeable and can be used in a selected embodiment, even if not specifically shown or described. The same may also be varied in many ways. Such variations are not to be regarded as a departure from the disclosure, and all such modifications are intended to be included within the scope of the disclosure.

What is claimed is:

1. An implantable electrically conductive device comprising:
   a flexible, electrically conductive, implantable region that comprises a nanocomposite material comprising a plurality of nanoparticles selected from the group consisting of: gold nanoparticles, carbon nanotubes, and combinations thereof.

2. The implantable electrically conductive device of claim 1, wherein the flexible, electrically conductive, implantable region is a structure formed by the nanocomposite material that comprises a plurality of carbon nanotubes.

3. The implantable electrically conductive device of claim 1, wherein the flexible, electrically conductive, implantable region has a surface coating comprising the nanocomposite material that comprises a plurality of gold nanoparticles.

4. The implantable electrically conductive device of claim 1, wherein the flexible, electrically conductive, implantable region has at least one dimension of less than or equal to about 10 µm.

5. The implantable electrically conductive device of claim 4, wherein the at least one dimension is a first dimension and the flexible, electrically conductive, implantable region has a second distinct dimension of less than or equal to about 50 µm.

6. The implantable electrically conductive device of claim 1, wherein the flexible, electrically conductive, implantable region has a resistivity of less than or equal to about $1 \times 10^{-5}$ Ohm·m.

7. The implantable electrically conductive device of claim 1, wherein the flexible, electrically conductive, implantable region has an electrical conductivity of greater than or equal to about $1 \times 10^5$.

8. The implantable electrically conductive device of claim 7, wherein the flexible, electrically conductive, implantable region has a charge storage capacity of greater than or equal to about 5 mC/cm$^2$ from −0.9 to 0.5 V.

9. The implantable electrically conductive device of claim 1, wherein the flexible, electrically conductive, implantable region forms a microelectrode.

10. The implantable electrically conductive device of claim 1, wherein the nanocomposite material further comprises a matrix material selected from a group consisting of: poly(dimethyldiallylammonium) chloride (PDDA), poly(vinyl alcohol), poly(styrene sulfonate) (PSS), chitosan (CH), and combinations thereof.

11. The implantable electrically conductive device of claim 1, wherein the device is separably coupled to a shuttle by frozen water, wherein the shuttle facilitates implantation of the device.

12. An implantable electrically conductive device comprising:
a nanocomposite material disposed on an implantable region of the implantable electrically conductive device that comprises a plurality of gold nanoparticles, wherein the implantable region of the electrically conductive device is flexible and has at least one dimension of less than or equal to about 10 μm.

13. The implantable electrically conductive device of claim 12, wherein the nanocomposite material is a coating on the implantable region.

14. The implantable electrically conductive device of claim 12, wherein the implantable electrically conductive device forms a microelectrode.

15. The implantable electrically conductive device of claim 12, wherein the implantable electrically conductive device is a neural prosthesis.

16. The implantable electrically conductive device of claim 12, wherein the nanocomposite material further comprises a matrix material selected from a group consisting of: poly(dimethyldiallylammonium) chloride (PDDA), chitosan (CH), and combinations thereof.

17. A method of making a nanocomposite material for an implantable device, comprising:
contacting a region of a surface of an implantable component with a polyelectrolyte to generate a monolayer of the polyelectrolyte; and
contacting the region of the surface of the implantable component having the monolayer of the polyelectrolyte disposed thereon with a solution comprising a plurality of gold nanoparticles so that the nanoparticles overlie the monolayer of the polyelectrolyte to form a nanocomposite coating over the region of the surface of the implantable component.

18. The method of claim 17, wherein the polyelectrolyte comprises poly(dimethyldiallylammonium) chloride (PDDA).

19. The method of claim 17, wherein the contacting of the region of a surface with the polyelectrolyte and the contacting with the plurality of gold nanoparticles steps are repeated multiple times.

20. A method of preparing an implantable electrically conductive device for implantation into a brain of an animal, the method comprising:
cooling a flexible, electrically conductive, implantable region of an electrically conductive device and a shuttle within a cold environment having a temperature of less than or equal to about 0° C., wherein the implantable region comprises a nanocomposite material comprising a plurality of nanoparticles selected from the group consisting of: gold nanoparticles, carbon nanotubes, and combinations thereof;
heating the shuttle and the flexible, electrically conductive, implantable region, so that water condenses on a first surface of the flexible, electrically conductive, implantable region and on a second surface of the shuttle;
bringing the first surface into contact with the second surface; and
cooling the shuttle and the implantable electrically conductive device to a temperature of less than or equal to about 0° C., so as to form a neural prosthetic device assembly capable of implantation into the brain of the animal.

* * * * *